(12) United States Patent
Jung et al.

(10) Patent No.: US 9,770,451 B2
(45) Date of Patent: Sep. 26, 2017

(54) COMPOSITION INCLUDING ATM INHIBITOR FOR REDUCING CELLULAR SENESCENCE AND USE OF THE COMPOSITION

(71) Applicant: Samsung Electronics Co., Ltd., Suwon-si, Gyeonggi-do (KR)

(72) Inventors: Chulwon Jung, Seoul (KR); Joontae Park, Seoul (KR); Hyuntae Kang, Seoul (KR); Sangchul Park, Seongnam-si (KR); Hyojei Choi, Seongnam-si (KR); Kobong Choi, Osan-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/796,677

(22) Filed: Jul. 10, 2015

(65) Prior Publication Data
US 2016/0113935 A1   Apr. 28, 2016

(30) Foreign Application Priority Data

Oct. 27, 2014   (KR) .................. 10-2014-0146436

(51) Int. Cl.
*A61K 31/5377* (2006.01)
*A61K 31/517* (2006.01)
*G01N 33/50* (2006.01)
*A61K 31/00* (2006.01)

(52) U.S. Cl.
CPC .......... *A61K 31/5377* (2013.01); *A61K 31/00* (2013.01); *A61K 31/517* (2013.01); *G01N 33/502* (2013.01)

(58) Field of Classification Search
CPC .......................... A61K 31/5377; A61K 31/517
See application file for complete search history.

(56) References Cited

U.S. PATENT DOCUMENTS

| | | |
|---|---|---|
| 7,429,660 B2 | 9/2008 | Smith et al. |
| 8,354,384 B2 | 1/2013 | Slack et al. |
| 8,476,259 B2 | 7/2013 | Fong |
| 8,673,840 B2 | 3/2014 | Chudzinski-Tavassi et al. |
| 2004/0014701 A1 | 1/2004 | O'Connor et al. |
| 2007/0049588 A1 | 3/2007 | Smith et al. |
| 2007/0099186 A1 | 5/2007 | D'Adda Di Fagagna et al. |
| 2008/0279866 A1 | 11/2008 | Iacomini et al. |
| 2009/0043091 A1 | 2/2009 | Smith et al. |
| 2010/0260733 A1 | 10/2010 | Qi |
| 2012/0010196 A1 | 1/2012 | Qin et al. |
| 2013/0338212 A1 | 12/2013 | Gollin et al. |
| 2014/0148496 A1 | 5/2014 | Desai |
| 2015/0246946 A1 | 9/2015 | Joseph et al. |
| 2016/0095864 A1 | 4/2016 | Park et al. |

FOREIGN PATENT DOCUMENTS

| | | |
|---|---|---|
| KR | 2016-0040932 A | 4/2016 |
| WO | WO 2014-055039 A | 4/2014 |

OTHER PUBLICATIONS

D'Adda Di Fagagna et al., "A DNA damage checkpoint response in telomere-initiated senescence", *Nature*, 426: 194-198 (2003).
Golding et al., "Improved ATM kinase inhibitor KU-60019 radiosensitizes glioma cells, compromises insulin, AKT and ERK prosurvival signaling, and inhibits migration and invasion", *Molecular Cancer Therapy*, 8(10): 2894-2902 (2009).
Li et al., "The ATM inhibitor KU-55933 Suppresses Cell Proliferation and Induces Apoptosis by Blocking Akt in Cancer Cells with Overactivated Akt", *Molecular Cancer Therapeutics*, 9(1): 113-125 (2010).
Vecchio et al., "Predictability, efficacy and safety of radiosensitization of glioblastoma-initiating cells by the ATM inhibitor KU-60019", *International Journal of Cancer*, 135: 479-491 (2014).

*Primary Examiner* — James D Anderson
(74) *Attorney, Agent, or Firm* — Leydig, Voit & Mayer, Ltd.

(57) ABSTRACT

A composition including an ataxia telangiectasia mutated (ATM) inhibitor for reducing cellular senescence, a method of reducing cellular senescence in a mammal, and a method of treating a symptom associated with cellular senescence in a mammal.

2 Claims, 33 Drawing Sheets

COMPOSITION INCLUDING ATM INHIBITOR FOR REDUCING CELLULAR SENESCENCE AND USE OF THE COMPOSITION

RELATED APPLICATION

This application claims the benefit of Korean Patent Application No. 10-2014-0146436, filed on Oct. 27, 2014, in the Korean Intellectual Property Office, the entire disclosure of which is hereby incorporated by reference.

BACKGROUND

1. Field

The present disclosure relates to a composition for reducing cellular senescence, a method of reducing cellular senescence in a mammal, and a method of treating a symptom associated with cellular senescence in a mammal.

2. Description of the Related Art

Senescence may be defined as a permanent halt in cell division. Replicative senescence or cellular senescence is observed as a model for aging at a cellular level. When cells are consecutively cultured, the cells are divided a number of times, but the cells are no longer divided according to cellular aging. The senescent cells actually have resistibility to programmed cell death, and in some cases, the senescent cells are maintained in a non-dividing state for years.

Ataxia telangiectasia mutated (ATM) is a serine/threonine protein kinase that is recruited and activated by DNA double-strand breaks. The ATM phosphorylates several key proteins that initiate activation of a DNA damage checkpoint, leading to cell cycle arrest, DNA repair, or cellular apoptosis. Several of these targets, including p53, CHK2, and H2AX, are tumor suppressors. The protein is named for the disorder ataxia telangiectasia caused by mutations of the ATM. The ATM belongs to the superfamily of phosphatidylinositol 3-kinase-related kinases (PIKKs). The PIKK superfamily includes six serine/threonine protein kinases that show a sequence similarity to a phosphatidylinositol 3-kinase (PI3K).

There remains a demand for a composition and a method for reducing cellular senescence.

SUMMARY

Provided is a composition comprising an ATM inhibitor, which is useful for reducing cellular senescence.

Also provided is a method of reducing cellular senescence, or treating a symptom associated with cellular senescence, in a mammal, the method comprising administering an ATM inhibitor to the mammal.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
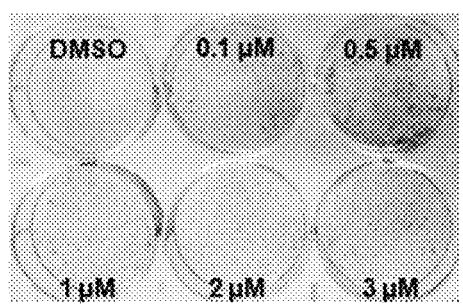
FIG. 1 is a view showing experimental results that confirm cell proliferation and formation of cell colonies according to various concentrations of ataxia telangiectasia mutated (ATM)-kinase inhibitor, KU-60019.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items.

Additional aspects will be set forth in part in the description which follows and, in part, will be apparent from the description, or may be learned by practice of the presented exemplary embodiments.

According to an aspect of an exemplary embodiment, provided is a composition for reducing cellular senescence, wherein the composition comprises an ataxia telangiectasia mutated (ATM) inhibitor as an effective ingredient.

ATM is a serine/threonine protein kinase that is recruited and activated by DNA double-strand breaks. The ATM phosphorylates several key proteins that initiate activation of a DNA damage checkpoint, leading to cell cycle arrest, DNA repair, or cellular apoptosis. Several of these targets, including p53, CHK2, and H2AX, are tumor suppressors. The protein is named for the disorder ataxia telangiectasia caused by mutations of the ATM. The ATM gene encodes a 350 kDa protein consisting of 3056 amino acids. The ATM belongs to the superfamily of phosphatidylinositol 3-kinase-related kinases (PIKKs). The PIKK superfamily includes six serine/threonine protein kinases that show a sequence similarity to a phosphatidylinositol 3-kinase (PI3K). Human ATM may have an amino acid sequence of NP_000042, the amino acid sequence may be encoded by NM_000051.

Mouse ATM may have an amino acid sequence of NP_031525, and the amino acid sequence may be encoded by NM_007499.

The ATM inhibitor may be any pharmaceutically acceptable compound that is known for inhibiting the ATM. Regarding a mechanism of the ATM inhibitor, the ATM inhibitor may be specific to (e.g., specifically bind) the ATM.

The ATM inhibitor may include a compound represented by Formula 1 below:

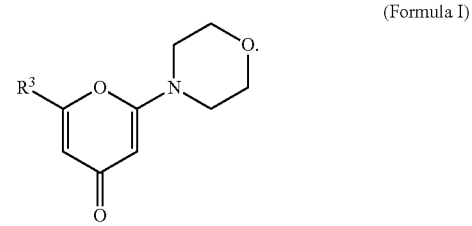

(Formula I)

In Formula I, $R^3$ may be a first phenyl group attached to an optionally substituted second phenyl group by a first bridge group that is selected from —S—, —S(=O)—, —S(=O)$_2$—, —O—, and —CR$^{C1}$R$^{C2}$—; the first phenyl group and the second phenyl group may be optionally further linked with each other by a second bridge group that is selected from —S—, —S(=O)—, —S(=O)$_2$—, —O—, —CR$^{C1}$R$^{C2}$—, —CR$^{C1}$R$^{C2}$CR$^{C1}$R$^{C2}$—, —C=O—, —CR$^{C1}$R$^{C2}$S—, —CR$^{C1}$R$^{C2}$O—, —SCR$^{C1}$R$^{C2}$—, —OCR$^{C1}$R$^{C2}$—, —R$^{C1}$=CR$^{C2}$—, and a single bond, wherein the second bridge group is bound adjacent to the first bridge group on both first and second phenyl groups so as to form an optionally substituted $C_5$-$C_7$ ring fused to both first and second phenyl groups, and the first phenyl group may be further optionally substituted;

$R^{C1}$ and $R^{C2}$ may be independently selected from a hydrogen, a hydroxyl group, a halo group, a cyano group, a nitro group, a halo-($C_1$-$C_7$ alkyl) group, and a $C_1$-$C_7$ alkyl group, wherein the first phenyl group in $R^3$ may optionally have a substituent selected from the group consisting of an amino group, a hydroxy group, a halo group, a cyano group, a $C_1$-$C_7$ alkyl group, a halo-($C_1$-$C_7$ alkyl) group, a nitro group, and a $C_1$-$C_7$ acyl group; and wherein the second phenyl group in $R^3$ may optionally have a substituent selected from the group consisting of an amino group, a hydroxyl group, a halo group, a cyano, $C_1$-$C_7$ alkyl group, a halo-($C_1$-$C_7$ alkyl) group, a nitro group, a $C_1$-$C_7$ acyl amino group, and

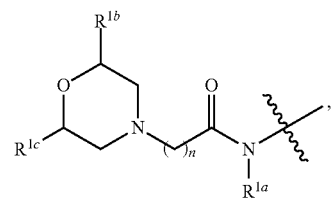

wherein each of $R^{1a}$, $R^{1b}$, and $R^{1c}$ is independently selected a hydrogen, a halo group, a cyano, a halo-($C_1$-$C_7$ alkyl) group, or a $C_1$-$C_7$ alkyl group, and n is an integer of 1 to 6.

In an exemplary embodiment, in $R_3$, the first phenyl group is an unsubstituted phenyl group, the first bridge group is —CH$_2$—, the second bridge group is —S—, and the second phenyl group is substituted with

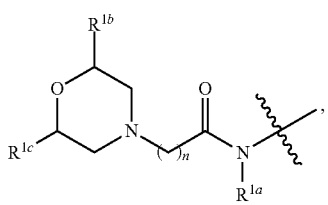

wherein each of $R^{1a}$, $R^{1b}$, and $R^{1c}$ is independently a hydrogen, a halo, a cyano, a halo-($C_1$-$C_7$ alkyl) group, or a $C_1$-$C_7$ alkyl group, and n is integer of 1 to 6.

In an exemplary embodiment, in $R_3$, the first phenyl group is an unsubstituted phenyl group, the first bridge group is —S—, and the second bridge group is —S—.

As used herein, the term "$C_1$-$C_7$ alkyl group", pertains to a monovalent moiety obtained by removing a hydrogen atom from a $C_1$-$C_7$ hydrocarbon compound having from 1 to 7 carbon atoms, which may be aliphatic or alicyclic, or a combination thereof, and which may be saturated, partially unsaturated, or fully unsaturated.

Examples of saturated linear $C_1$-$C_7$ groups include but are not limited to methyl, ethyl, n-propyl, n-butyl, and n-pentyl (amyl).

Examples of saturated branched $C_1$-$C_7$ groups include but are not limited to iso-propyl, iso-butyl, sec-butyl, tert-butyl, and neo-pentyl.

Examples of saturated alicyclic $C_1$-$C_7$ alkyl groups (also referred to as "$C_3$-$C_7$ cycloalkyl" groups) include but are not limited to, groups such as cyclopropyl, cyclobutyl, cyclopentyl, and cyclohexyl, as well as substituted groups (e.g., groups which comprise such groups), such as methylcyclopropyl, dimethylcyclopropyl, methylcyclobutyl, dimethylcyclobutyl, methylcyclopentyl, dimethylcyclopentyl, methylcyclohexyl, dimethylcyclohexyl, cyclopropylmethyl, and cyclohexylmethyl.

Examples of unsaturated $C_1$-$C_7$ alkyl groups which have one or more carbon-carbon double bonds (also referred to as "$C_2$-$C_7$ alkenyl" groups) include but are not limited to, ethenyl (vinyl, —CH=$CH_2$), 2-propenyl (allyl, —CH—CH=$CH_2$), isopropenyl (—C($CH_3$)=$CH_2$), butenyl, pentenyl, and hexenyl.

Examples of unsaturated $C_1$-$C_7$ alkyl groups which have one or more carbon-carbon triple bonds (also referred to as "$C_2$-$C_7$ alkynyl" groups) include but are not limited to ethynyl and 2-propynyl (i.e., propargyl).

Examples of unsaturated alicyclic (carbocyclic) $C_1$-$C_7$ alkyl groups which have one or more carbon-carbon double bonds (also referred to as "$C_3$-$C_7$ cycloalkenyl" groups) include but are not limited to, unsubstituted groups such as cyclopropenyl, cyclobutenyl, cyclopentenyl, and cyclohexenyl, as well as substituted groups (e.g., groups which comprise such groups) such as cyclopropenylmethyl and cyclohexenylmethyl.

As used herein, the phrase "amino group" is as follows: —$NR^1R^2$, wherein $R^1$ and $R^2$ are independently amino substituents, for example, hydrogen, a $C_1$-$C_7$ alkyl group (also referred to as $C_1$-$C_7$ alkylamino or di-$C_1$-$C_7$ alkylamino) or, in the case of a "cyclic" amino group, $R^1$ and $R^2$, taken together with the nitrogen atom to which they are attached, form a heterocyclic ring having from 4 to 8 ring atoms. Examples of amino groups include but are not limited to, —$NH_2$, —$NHCH_3$, —$NHC(CH_3)_2$, —$N(CH_3)_2$, —$N(CH_2CH_3)_2$, and —NHPh. Examples of cyclic amino groups include but are not limited to, aziridino, azetidino, pyrrolidino, piperidino, piperazino, morpholino, and thiomorpholino.

As used herein, the phrase "hydroxyl group" refers to —OH, the phrase "halo group" refers to —F, —Cl, —Br, and —I, and the phrase "nitro group" refers to —$NO_2$, and definition of the cyano group refers to —NC.

As used herein, the phrase "acylamino group" is as follows: —$NR^1C(=O)R^2$, wherein $R^1$ is an amide substituent, for example, a hydrogen, a $C_1$-$C_7$ alkyl group, and $R^2$ is an acyl substituent, for example, a $C_1$-$C_7$ alkyl group. Examples of the acylamino groups include but are not limited to —NHC(=O)$CH_3$ and —NHC(=O)$CH_2CH_3$. $R^1$ and $R^2$ may together form a cyclic structure, as in, for example, succinimidyl, maleimidyl, and phthalimidyl.

As used herein, the phrase "acyl (keto) group" is as follows: —C(=O)R, wherein R is an acyl substituent, for example, a $C_1$-$C_7$ alkyl group. Examples of the acyl groups include but are not limited to, —C(=O)$CH_3$ (acetyl), —C(=O)$CH_2CH_3$ (propionyl), and —C(=O)C($CH_3$)$_3$ (butyryl).

The ATM inhibitor may be, for example, KU-60019, KU-55933, CP-466722, pharmaceutically acceptable salts thereof, stereoisomers thereof, or a combination thereof. The term "ATM inhibitor" as used herein refers to a substance that acts as an inhibitor of ATM kinase activity. KU-60019 may have a structure represented by Formula II below.

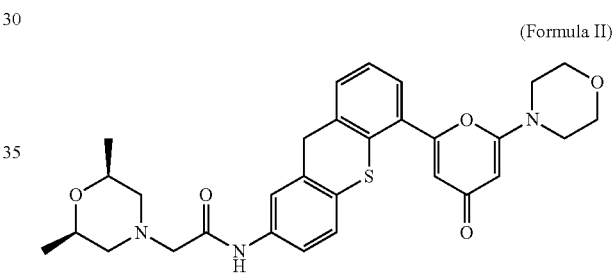

(Formula II)

KU-60019 (2-((2S,6R)-2,6-dimethylmorpholino)-N-(5-(6-morpholino-4-oxo-4H-pyran-2-yl)-9H-thioxanthen-2-yl)acetamide) is about 10-fold more effective than KU-55933 at blocking radiation-induced phosphorylation of key ATM targets in human glioma cells. KU-60019 is a highly effective radiosensitizer in human glioma cells. KU-60019 may be synthesized or purchased from a commercial supplier.

KU-55933 (2-(4-morpholinyl)-6-(1-thianthrenyl)-4H-pyran-4-one) may have a structure represented by Formula III below. KU-55933 may be synthesized or purchased from a commercial supplier.

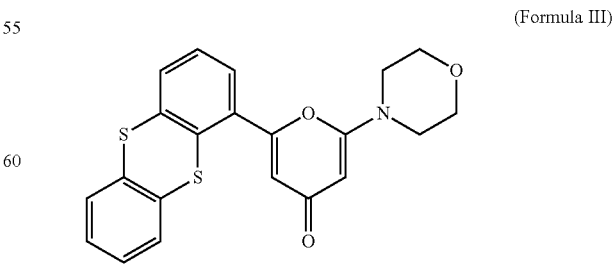

(Formula III)

CP-466722 may have a structure represented by Formula IV below. CP-466722 (2-(6,7-dimethoxyquinazolin-4-yl)-5-

(pyridin-2-yl)-2H-1,2,4-triazol-3-amine) may be synthesized or purchased from a commercial supplier.

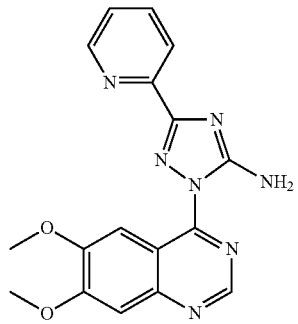

(Formula IV)

A reduction in cellular senescence may refer to delay or prevention of cellular senescence, or reversion of a senescent cell to a younger cell state (e.g., a cell state similar to that of a pre-senescent cell).

A reduction in cellular senescence may refer to at least one of increase in proliferation of a cell, reduction in accumulation of lipofuscin, reduction in activity of β-galactosidase, reduction in the number of mitochondrial reactive oxygen species (ROS), increase in mitochondrial membrane potential, and reduction of the G0 and/or G1 phase of the cell cycle. The cell mentioned herein may be muscular cells including myoblast, fibroblast, early senescent cells, or nerve cells. The early senescent cells may be derived from a patient with progeria. Progeria may include Hutchinson-Gilford progeria or Werner syndrome.

The composition may be used to treat a symptom associated with cellular senescence. For example, the symptom associated with cellular senescence may include wrinkle, wound healing declines, sarcopenia, early senescent symptom (e.g., Hutchinson-Gilford progeria syndrome), or a combination thereof. The symptom associated with cellular senescence may include a symptom associated with lipofuscin accumulation. The symptom associated with lipofuscin accumulation includes neuronal ceroid lipofuscinoses (NCL), age-related macular degeneration, neurofibrillary tangles, brown atrophy of the heart, Alzheimer's disease, Parkinson's disease, amyotrophic lateral sclerosis (ALS), acromegaly, denervation atrophy, lipid myopathy, or chronic obstructive pulmonary disease (COPD). In addition, the symptom associated with cellular senescence includes a disease that may be caused by an increase in mitochondrial ROS, reduction in mitochondrial membrane potential, or a combination thereof including a mitochondrial damage. In addition, the symptom associated with cellular senescence includes a disease that may be caused by increased activity of β-galactosidase in a cell.

The ATM kinase inhibitor may be prepared in the form of a pharmaceutically acceptable salt. The pharmaceutically acceptable salt may include, for example, an acid-addition salt that is typically used in the pharmaceutical field with respect to a disease associated with cellular senescence. Examples of the acid-addition salt include salts derived from inorganic acids, such as hydrochloric acid, hydrobromic acid, sulfuric acid, sulfamic acid, phosphoric acid, and nitric acid, and salts derived from acetic acid, propionic acid, succinic acid, glycolic acid, stearic acid, citric acid, maleic acid, malonic acid, methanesulfonic acid, tartaric acid, malic acid, phenylacetic acid, glutamic acid, benzoic acid, salicylic acid, 2-acetoxybenzoic acid, fumaric acid, toluenesulfonic acid, oxalic acid, or trifluoroacetic acid. In addition, the pharmaceutically acceptable salt may be prepared in the form of typical metal salts, and for example, metal salts include salts derived from metal, such as lithium, sodium, potassium, magnesium, or calcium. The acid-addition salt or metal salt may be prepared according to a method known in the art.

The ATM-kinase inhibitor may be also prepared in the form of a solvate. The term "solvate" used herein refers to a complex or an aggregate of at least one solute molecule, e.g., the ATM-kinase inhibitor or the pharmaceutically acceptable salt thereof, and at least one solute molecule. The solvate may include, for example, a complex or an aggregate formed using water, methanol, ethanol, isopropanol, or acetic acid.

The ATM-kinase inhibitor may be also prepared in the form of a stereoisomer. The stereoisomer may include all types of stereoisomers including an enantiomer and a diastereomer. The ATM-kinase inhibitor may be prepared in a stereoisomerically pure form or a mixture of at least one stereoisomer, such as a racemic mixture. Separation of a particular stereoisomer may be performed according to a method known in the art.

In the composition, the cells may be cells of a mammal including a human. The mammal may have a disease associated with cellular senescence.

The composition may further include a pharmaceutically acceptable carrier. In the composition, the term "pharmaceutically acceptable carrier" used herein generally refers to an inert material, i.e., a material used in combination with an active ingredient to assist the application of the active ingredient. The carrier may include a pharmaceutically acceptable excipient, additive, or diluent. The carrier may include at least one selected from, for example, a filler, a binder, a disintergrant, a buffer, a preservative, an antioxidant, a lubricant, a flavoring agent, a thickener, a coloring agent, an emulsifier, a suspending agent, a stabilizer, and an isotonic agent.

The composition may contain the ATM-kinase inhibitor, the pharmaceutically acceptable salt thereof, or the solvate in a "therapeutically effective amount". In the composition, the term "therapeutically effective amount" used herein refers to an amount that is sufficient enough to indicate an effect (e.g., an increase in cellular proliferation or a reduction in accumulation of lipofuscin) on treatment when administered to a subject in need of the treatment. The term "treatment" used herein refers to a practice of treating disease or a medical symptom, e.g., a disease associated with cellular senescence, in a subject such as a mammal including a human, and examples of the treatment are as follows: (a) prevention of the occurrence of a disease or a medical symptom, and that is, prophylactic treatment of a patient; (b) alleviation of a disease or a medical symptom, and that is, involvement of removal or recovery of a disease or a medical symptom in a patient; (c) inhibition of a disease or a medical symptom, and that is, involvement of delaying or stopping a disease or a medical symptom in a subject; or (d) reduction of a disease or a medical symptom in a subject. The "effective amount" may be appropriately selected by one of ordinary skill in the art. For example, the "effective amount" of the ATM inhibitor may be in a range from about 0.01 mg to about 10,000 mg, about 0.1 mg to about 1,000 mg, about 1 mg to about 100 mg, about 0.01 mg to about 1,000 mg, about 0.01 mg to about 100 mg, about 0.01 mg to about 10 mg, or about 0.01 mg to about 1 mg.

The composition may be administered orally to a subject, or parenterally to a subject in a way of intravenous, intraperitoneal, subcutaneous, rectal, and topical administration. Therefore, the composition may be formulated in various forms including tablets, capsules, aqueous solutions, or suspensions. In the case of tablet formulation for oral use, excipients, such as lactose or corn starch, and a lubricant, such as magnesium stearate, may be added to the composition. In the case of capsule formulation for oral use, lactose and/or dry corn starch may be used as a diluent in the composition. When an aqueous suspension for oral use is required, an active ingredient may be used in combination with an emulsifier and/or a suspending agent. If necessary, a particular sweetening agent and/or a flavoring agent may be added to the composition. In the case of neural, intramuscular, intraperitoneal, subcutaneous, and intravenous administration, a sterile solution of an active ingredient is typically prepared, thereby appropriately adjusting and buffering pH of the solution. In the case of intravenous administration, the total concentration of solutes is adjusted to render the formulation isotonicity. The composition may be prepared in prepared in the form of an aqueous solution containing a pharmaceutically acceptable diluent having a pH of 7.4 as of salt water. The aqueous solution may be introduced into muscle or nerve blood flow of a patient by local bolus injection.

The term "cellular senescence" or "senescence of a cell" used herein refers to, as compared with a reference cell (e.g., a known non-senescent cell of the same cell type), at least one of reduction in proliferation of a cell, accumulation of lipofuscin, increase in β-galactosidase activity, increase in the number of mitochondrial ROS, reduction in mitochondrial membrane potential, and increase in the G0 and/or G1 phase of the cell cycle, or to a process causing phenomena above. The term "young cell" used herein refers to, as compared with a reference cell (e.g., a known senescent cell of the same type), a cell with at least one of increased proliferation of a cell, decreased accumulation of lipofuscin, decreased activity of β-galactosidase, decreased number of mitochondrial ROS, increased mitochondrial membrane potential, and decreased G0 and/or G1 phase of the cell cycle. The term "reference cell" refers to a cell, for example, a fibroblast derived from a person aged 18 to 25, 18 to 23, or 18 to 20 who are normal and healthy. The reference cell may be a fibroblast cell, kidney cell, pancreas cell, or retinal cell.

The composition may be used in combination with at least one additional therapeutic agent to treat a disease associated with cellular senescence. Alternatively, the composition may be free of other active ingredients used to treat a disease associated with cellular senescence other than the ATM-kinase inhibitor, the pharmaceutically acceptable salt thereof, or the solvate thereof.

According to an aspect of another exemplary embodiment, a method of reducing cellular senescence in a mammal includes: administering an effective amount of the ATM-kinase inhibitor to a mammal to reduce cellular senescence.

Here, the "ATM-kinase inhibitor", "the reduction in cellular senescence", and "the mammal" used regarding the method are defined the same as described above. The effective amount refers to "an amount sufficient enough to reduce cellular senescence" when administered to a subject having cellular senescence. The administration refers to administration of the composition to a mammal, wherein the composition includes "the ATM-kinase inhibitor, the pharmaceutically acceptable salt thereof, or the solvate thereof".

According to an aspect of another exemplary embodiment, provided is a method for treating a symptom associated with cellular senescence in a mammal, wherein said method includes: administering an effective amount of the ATM-kinase inhibitor to a mammal to treat the symptom associated with cellular senescence.

According to an aspect of another exemplary embodiment, provided is a method for treating a symptom associated with the accumulation of lipofuscin in a mammal, wherein said method includes: administering an effective amount of the ATM-kinase inhibitor to a mammal to treat the symptom associated with the accumulation of lipofuscin.

Here, the "ATM-kinase inhibitor," "the reduction in cellular senescence," and "the mammal" used regarding the method are the same as described above. The effective amount refers to "an amount sufficient enough to reduce cellular senescence" when administered to a subject having cellular senescence. The effective amount also refers to "an amount sufficient enough to reduce the accumulation of lipofuscin" when administered to a subject having the accumulation of lipofuscin. The accumulation of lipofuscin may be an accumulation of lipofuscin within a cell such as fibroblast, myoblast, kidney cell, or pracreas cell. The administration refers to administration, to a mammal, the composition including "the ATM-kinase inhibitor, the pharmaceutically acceptable salt thereof, or the solvate thereof".

In regard to the administration, one of ordinary skill in the art may appropriate select a route of the administration depending on a patient's condition. The administration may be oral, parenteral, or topical administration. The administration may be topically applied to a tissue consisting of senescent cells. The administration may be topically applied to a skin tissue, a muscle tissue, or a nerve tissue.

The administration amount may vary as described above, according to a variety of factors, such as a patient's condition, an administration route, or physician's determination. The effective administration amount may be estimated by a dose-response curve obtained in vitro or from an animal model test. The ratio or concentration of the compound disclosed herein may be contained in the composition to be administered according to chemical properties, the route of administration, or therapeutic amounts. The administration amount may be effective in a subject when administered in a range from about 0.001 to about 10,000 mg/kg body weight per day, about 0.001 to about 1 mg/kg body weight per day, about 0.01 to about 10,000 mg/kg body weight per day, about 0.1 to about 1,000 mg/kg body weight per day, about 0.1 to about 500 mg/kg body weight per day, about 1 to about 100 mg/kg body weight per day, about 0.01 to about 1,000 mg/kg body weight per day, about 0.01 to about 100 mg/kg body weight per day, about 0.01 to about 10 mg/kg body weight per day, or about 0.01 to about 1 mg/kg body weight per day. Here, the administration amount may vary according to a subject's age, weight, susceptibility, or the symptoms a subject presents.

The method may further include measuring the doubling time of a cell, the amount of lipofuscin in a cell, β-galactosidase activity in a cell, the number of mitochondrial ROS in a cell, mitochondrial membrane potential, and the period of the G0 and/or G1 phase of the cell cycle for a cell. The method may further include comparing the resultant data of the measurement with that of a control cell, wherein the control cell is a reference cell. The reference cell may a known non-senescent cell of the same cell type. The term "reference cell" refers to a cell, for example, a fibroblast derived from a person aged 18 to 25, 18 to 23, or 18 to 20 who are normal and healthy. The reference cell may be a fibroblast cell, kidney cell, pancreas cell, or retinal cell. The method may further include determining that the cell is a senescent cell, when increased the doubling time of a cell, increased accumulation of lipofuscin in a cell, increased β-galactosidase activity in a cell, increased the number of mitochondrial ROS in a cell, decreased mitochondrial membrane potential, and increased the period of the G0 and/or G1 phase of the cell cycle for a cell is observed compared to the reference cell. The method may further include determining that the cell has an accumulation of lipofuscin, when increased amount of lipofuscin in a cell is observed compared to the reference cell.

According to an aspect of another exemplary embodiment, provided is a method of treating a wound in a mammal, the method comprising: administering an effective amount of an ataxia telangiectasia mutated (ATM) inhibitor to a mammal to treat the wound, wherein the ATM inhibitor is KU-60019, KU-55933, CP-466722, a pharmaceutically acceptable salt, a stereoisomer, or a combination thereof. In the method, the wound comprises a senescent cell. The wound may present on a skin with cut. In the method, the ATM inhibitor enhances closure of the wound and reduces the size of the wound.

The composition according to an aspect may be used to reduce cellular senescence, wherein the composition includes the ATM-kinase inhibitor, the pharmaceutically acceptable salt thereof, or the solvate thereof.

The method of reducing cellular senescence in a mammal according to another aspect may be used to efficiently reduce the cellular senescence in a mammal.

The method of treating a symptom associated with cellular senescence in a mammal according to another aspect may be used to treat the symptom associated with cellular senescence in a mammal.

The method of treating a symptom associated with the accumulation of lipofuscin in a mammal according to another aspect may be used to treat the symptom associated with the accumulation of lipofuscin in a mammal.

EXAMPLES

Hereinafter, the present invention will be described in further detail with reference to the following examples. These examples are for illustrative purposes only and are not intended to limit the scope of the present invention.

Example: (1) Influence of KU-60019 on Cell Proliferation of Senescent Fibroblasts (Passage 37)

A human fibroblast cell line was inoculated into a Dulbecco's Modified Eagle's medium (DMEM) containing 10% fetal bovine serum (FBS), 100 units/ml of penicillin, and 100 μg/ml of streptomycin (wherein these two antibiotics were purchased from Gibro-BRL, Grand Island, N.Y.), and then, cultured in a 5% $CO_2$ incubator at a temperature of 37° C. The fibroblast cell line (i.e., M11 strain) was a cell line derived from the foreskin of an 11-year-old boy. When the cells were grown to about 85% confluency in a plate, the cells were subjected to subculture. The early subculture was carried out at a split ratio of 1:4, and the late subculture was carried out at a split ratio of 1:2. When the cell doubling time was 14 days, the cells were considered to be senescent fibroblasts (passages 35 to 37).

To determine the optimal concentration upon the treatment with an ATM-kinase inhibitor KU-60019 (SELLECKCHEM, S1570, salt), the senescent fibroblasts (passage 37) were inoculated into each well of a 6-well plate at a concentration of 2,000 cells/well, and then, KU-60019 was added to each well of the 6-well plate (at a concentration of 0.1 μM, 0.5 μM, 1 μM, 2 μM, and 3 μM). In addition, as a negative control group, the cells were cultured under the same conditions as described above, except that a medium used herein contained a dimethyl sulfoxide (DMSO) (0.05 (v/v) %) medium. The medium containing ATM-kinase inhibitor, KU-60019, was replaced by a fresh medium containing KU-60019 once every 4 days. After a lapse of 4 days from addition of KU-60019, colonies formed on the medium were stained with 0.05% crystal violet dye.

FIG. 1 is a view showing experimental results that confirm cell proliferation and formation of cell colonies according to concentrations of the ATM-kinase inhibitor KU-60019.

As shown in FIG. 1, the ATM-kinase inhibitor KU-60019 produced best results in the cell proliferation and the formation of cell colonies at concentrations of 0.1 μM, 0.5 μM, and 2 μM. Among the concentrations of 0.1 μM, 0.5 μM, and 2 μM, which resulted in good cell proliferation and formation of cell colonies, the 0.5 μM concentration was selected as the most effective concentration, and then, was used in the subsequent experiments.

To quantitatively measure an extent of inducing the cell proliferation at the optimal concentrations of FIG. 1, the cells were inoculated into each well of a 96-well plate at a concentration of 2,000 cells/well. Afterwards, KU-60019 was added to each well at a 0.5 μM concentration, and then, as a negative control group, the cells were cultured under the same conditions as described above, except that a medium used herein contained DMSO (0.05 (v/v) %). To measure changes in the number of cells that were divided in the each cell of the 96-well plate, cell number was measured by the fluorescence intensity of SYBR green I nucleic acid gel stain (Molecular Probes, Eugene, Oreg.) using a fluorescence microplate reader (Fluostar from BMG, Durham, N.C.), according to an incubation time (4, 8, 12, 16 days). In FIG. 1, data was determined from twelve replicates (n=12).

Figure 2:
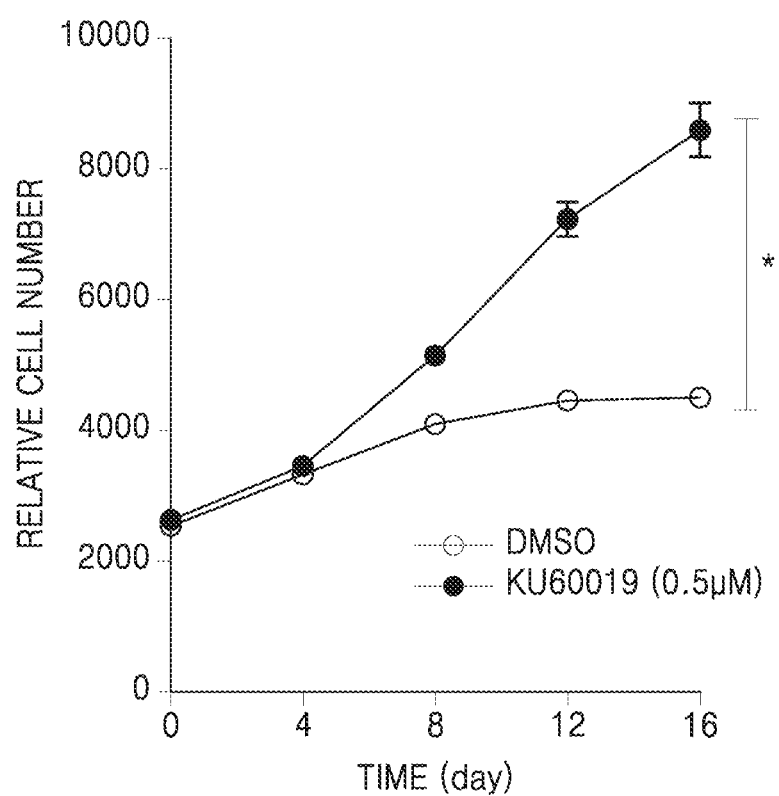
FIG. 2 is a graph displaying the number of senescent fibroblasts (passage 37) that are cultured in the presence of KU-60019.

FIG. 2 is a view showing the number of senescent fibroblasts (passage 37) that were cultured in the presence of KU-60019. Referring to FIG. 2, 0.5 μM of KU-60019 was added to the media, and the cells were cultured in a 5% $CO_2$ incubator at a temperature of 37° C. Each of the media was replaced by a fresh medium having a 0.5 μM concentration, once every 4 days. Here, the cells were used for the experiments in multiples of 12 (n=12). As shown in FIG. 2, in the case of culturing the cells for 16 days in the presence of the compound, KU-6001, the number of cells, compared to a control group, significantly increased. In FIG. 2, * indicates statistical significance (p<0.05). In FIG. 2, the vertical axis represents "relative" cell number, and that is, the relative concentration was obtained by a method of measuring amounts of DNA using SYBR Green to indirectly measure the number of cells based on the amounts of DNA.

In addition, to confirm whether the cells proliferated by the culture proliferate abnormally, for example, proliferate like cancer cells, a soft agar assay was carried out. First, the DMEM medium containing 10% FBS was mixed with a 1.6% agar medium at a ratio of 1:1, so as to prepare a medium containing 0.8% agar formulation to coat the bottom of each well of a 6-well plate. Afterwards, 2,500 cells were added to a medium containing KU-60019 (0.5 μM), and then, mixed with a 0.8% agar medium, resulting in a final concentration of 0.4%. 1 mL of a 0.4% agar medium was then spread over the 0.8% agar medium. The cells were cultured for 4 weeks in a $CO_2$ incubator at a temperature of 37° C., and to prevent the agar formulation from being dried, a fresh medium containing KU-60019 (0.5 µM) was added once every 4 days. As a control group, a 293T cell line (ATCC® CRL-11268™) from human embryonic kidney was used. In addition, as a negative control group, the cells were cultured under the same conditions as described above, except that a medium used herein contained DMSO (0.05 (v/v) %).

Figure 3:
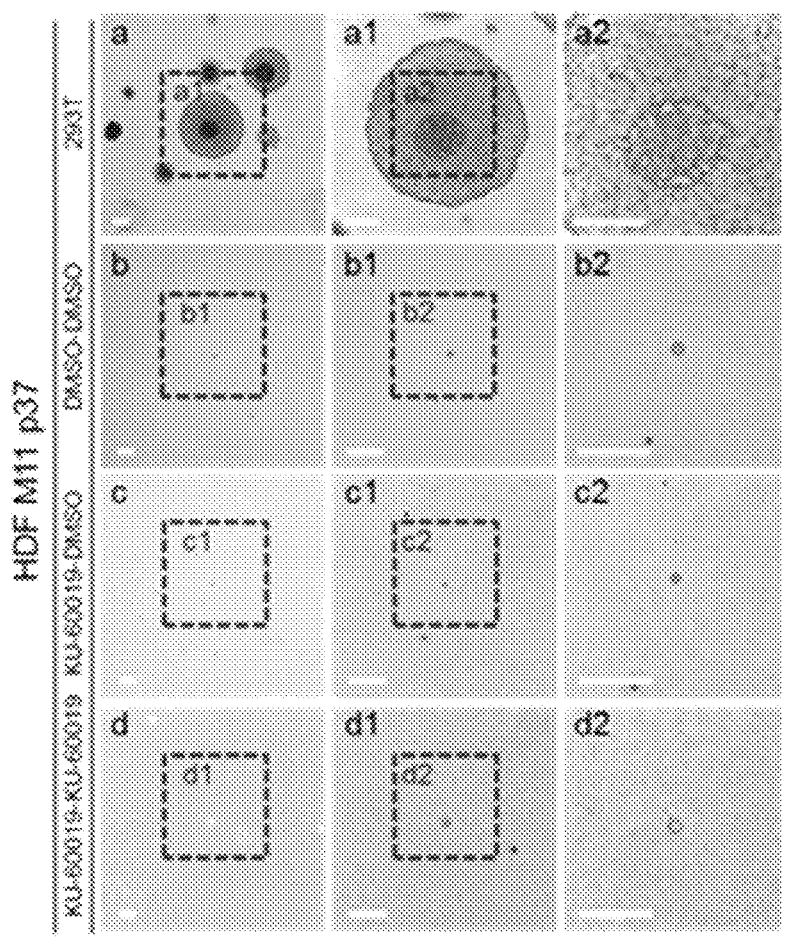
FIG. 3 is a view showing results of culturing cells in an agar medium in the presence of an ATM-kinase inhibitor KU-60019, in an agar medium.

FIG. 3 is a view showing results of culturing cells in an agar medium in the presence of the ATM-kinase inhibitor KU-60019. As shown in FIG. 3, colonies were formed in the 293T cells, which are cancer cells, while colonies were not formed in the other cells. To provide a better view of the colonies formed in part a of FIG. 3, a dashed square a1 was randomly selected, and then, the colony in the dashed square a1 was shown enlarged. To provide a better view of the colonies formed in the dashed square a1, a dashed square a2 was randomly selected, and then, the colony in the dashed square a2 was shown enlarged (at a scale bar 20 µm). The same procedure applies similarly to the remaining images b, c, and d. In FIG. 3, HDF M11 p37 refers to a human dermal fibroblast M11 strain, which is a sub-cultured fibroblast (passage 37). In FIG. 3, KU-60019-KU-60019 refers to a process of continuously adding KU-60019 to a medium and culturing for 28 days; KU-60019-DMSO refers to a process of adding KU-60019 to a medium and culturing for 14 days, removing KU-60019, and then, culturing the cells in the absence of KU-60019 for another 14 days; DMSO-DMSO refers to a condition where KU-60019 is not added at all and the cells cultured for 28 days. The 293T cells were cultured under the same condition as DMSO-DMSO, and then, applied to the soft agar assay.

(2) Influence of KU-60019 on Recovery of Senescent Fibroblasts (Passage 37) to Young Cells In addition, the influence of an ATM-kinase inhibitor KU-60019 on the expression of senescence-associated β-galactosidase (SA-β-gal) in the cells proliferated by the culture was confirmed by using a β-galactosidase staining kit (Cell Signaling Technology, #9860, Beverly, Mass.). According to the protocol of the manufacturer, a pH 6.0 X-gal chromogenic substrate was incubated overnight at a temperature of 37° C. to stain the cells having immobilized cell growth.

Figure 4:
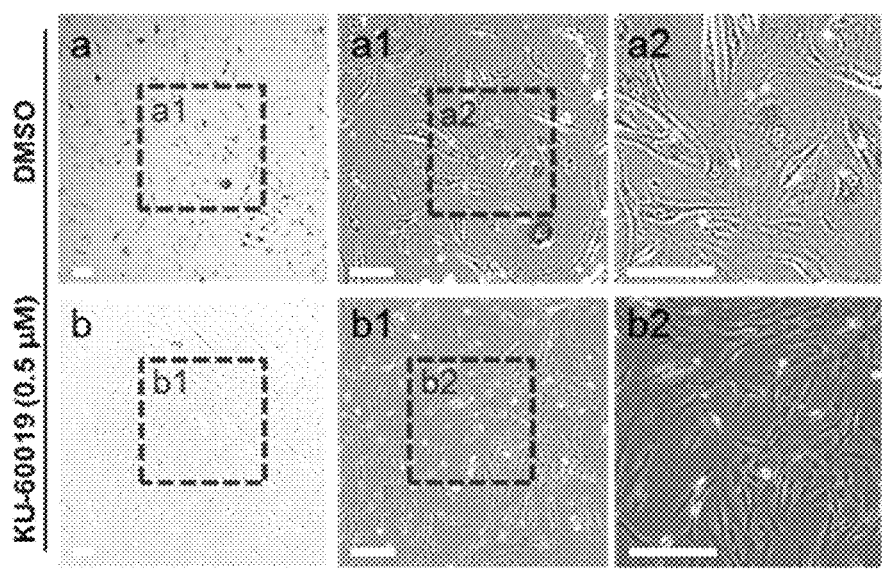
FIG. 4 is a view showing activity of SA-β-galactosidase of cells that are cultured in the presence of KU-60019 (0.5 μM)
Figure 5:
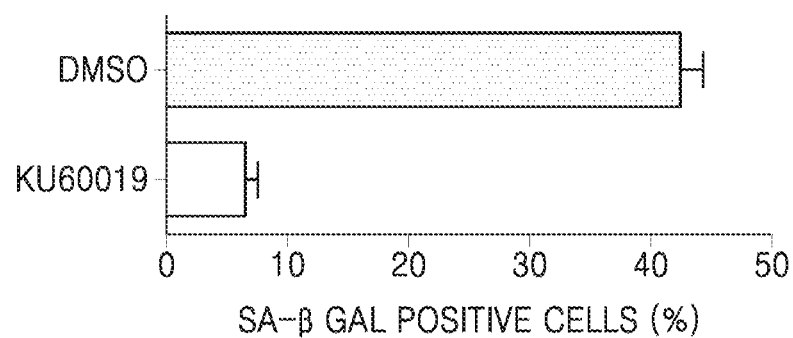
FIG. 5 is a graph showing a percentage of the cells having the activity of SA-β-galactosidase.

FIGS. 4 and 5 are each a view showing SA-β-gal activity of the cells that were cultured in the presence of KU-60019 (0.5 µM) (a and b of FIG. 4) and a graph showing a percentage of the cells having the SA-β-gal activity (FIG. 5). Referring to FIGS. 4, a, a1, and a2 show the cells using DMSO as a negative control group; and b, b1, and b2 show the cells treated with KU-60019 (0.5 µM). To provide a better view of the stained cells in the part a of FIG. 4, a dashed square a1 was randomly selected, and then, the stained cells in the dashed square a1 are shown enlarged. To provide a better view of the cells formed in the dashed square a1, a dashed square a2 was randomly selected, and then, the stained cells in the dashed square a2 are shown enlarged (at a scale bar 20 µm). The same procedure applies similarly to the image b.

As shown in FIGS. 4 and 5, the number of cells that express β-galactosidase, as compared to a control group (treatment with DMSO (0.05 (v/v) %)), significantly decreased in the presence of the compound, KU-60019.

Figure 6:
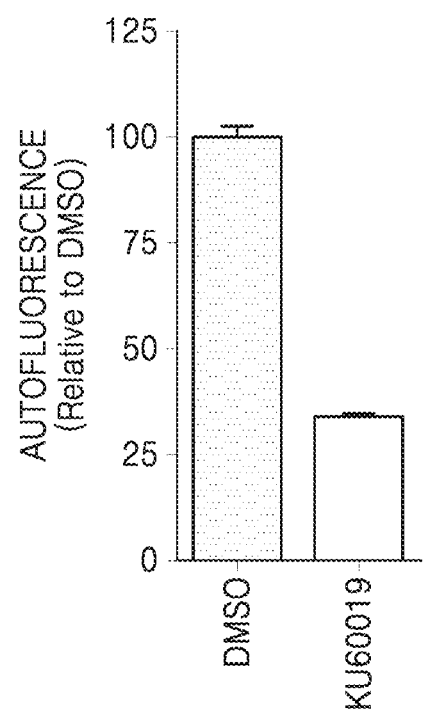
FIG. 6 is a graph showing lipofuscin measured in cells that are cultured in the presence of KU-60019.
Figure 7:
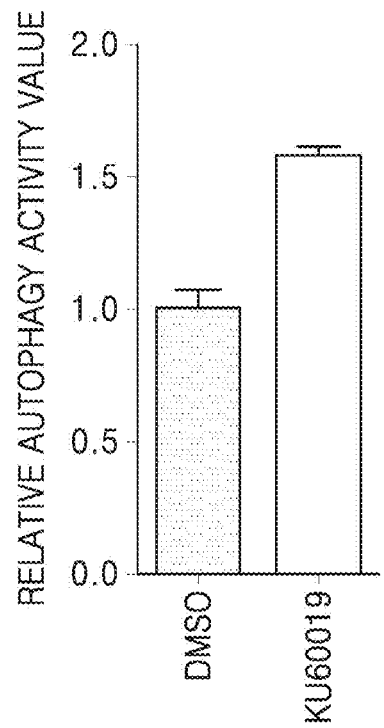
FIG. 7 is a graph showing autophagy activity values of cells that are cultured in the presence of KU-60019.

In addition, the amounts of lipofuscin in the cultured cells were measured. In the presence of KU-60019 (0.5 µM), the senescent cells (Passage 37) were cultured in a $CO_2$ incubator at a temperature of 37° C. for 3 to 4 weeks. The medium was replaced by a fresh medium containing KU-60019 (0.5 µM), once every 4 days. Lipofuscin is characterized by having autofluorescence capability, and in this regard, the cultured cells were irradiated with a wavelength of 488 nm by using an FACSCaliber (Beckton Dickinson), and then measured with radiation emitted from a wavelength of 520 nm. The results were analyzed using Cell Quest 3.2 software (Beckton Dickinson). FIG. 6 is a graph showing lipofuscin measured in the cells that were cultured in the presence of KU-60019. As shown in FIG. 6, the amount of lipofuscin, as compared to a control group, significantly decreased in the cells cultured in the presence of KU-60019. FIG. 7 is a graph showing autophagy activity value of the cells that were cultured in the presence of KU-60019.

As shown in FIG. 7, the autophagy activity value of the cells, compared to a control group, significantly increased in the cells that were cultured in the presence of KU-60019. The autophagy activity value was measured according to the protocol of the manufacturer using the Cyto-ID®Autophagy detection kit (Enzo Lifescience, ENZ-51031-K200). A dying reagent (477 nm laser excitable dye) used in the kit was specifically bound to a vacuole undergoing autophagy, thereby measuring an amount of the vacuole undergoing autophagy. The cultured cells were irradiated with a wavelength of 488 nm by using a FACSCaliber (Beckton Dickinson), and then, were measured with radiation emitted from a wavelength of 520 nm. The results were analyzed using Cell Quest 3.2 software (Beckton Dickinson).

In addition, in regard to the cells cultured as described above, the occurrence of mitochondrial damage to the cells was confirmed by using a well-known method measuring reactive oxygen species (ROS) and mitochondrial membrane potential.

ROS was measured according to the protocol of the manufacturer using a 0.2 µM MitoSOX™ Red mitochondrial superoxide indicator for live-cell imaging (Invitrogen, M36008) (hereinafter, referred to as "MitoSOX™ Red reagent"). In detail, 2 µL of the reagent that was stored in a 1,000-fold concentration was added to a 2 ml medium sufficiently enough to cover the cultured cells that were attached to a coverslip. While being protected from light, the cells were further incubated at a temperature of 37° C. for 30 minutes. The cultured cells were irradiated with a wavelength of 520 nm by using a FACSCaliber (Beckton Dickinson), and then, were measured with radiation emitted from a wavelength of 580 nm. The results were analyzed using Cell Quest 3.2 software (Beckton Dickinson). The MitoSOX™ Red reagent is a fluorogenic dye for highly selective detection of superoxides in mitochondrial in live cells. The MitoSOX™ Red reagent is live-cell permeant, and is rapidly and selectively targeted to the mitochondria. Once in the mitochondria, the MitoSOX™ Red reagent is oxidized by superoxide and exhibits red fluorescence. The MitoSOX™ Red reagent is easily oxidized by superoxide, but is not oxidized by other ROS or a reactive nitrogen species (RNS)-generation system. When the oxidation product of the reagent binds to a nucleic acid, the oxidation product may be highly fluorescent.

Figure 8:
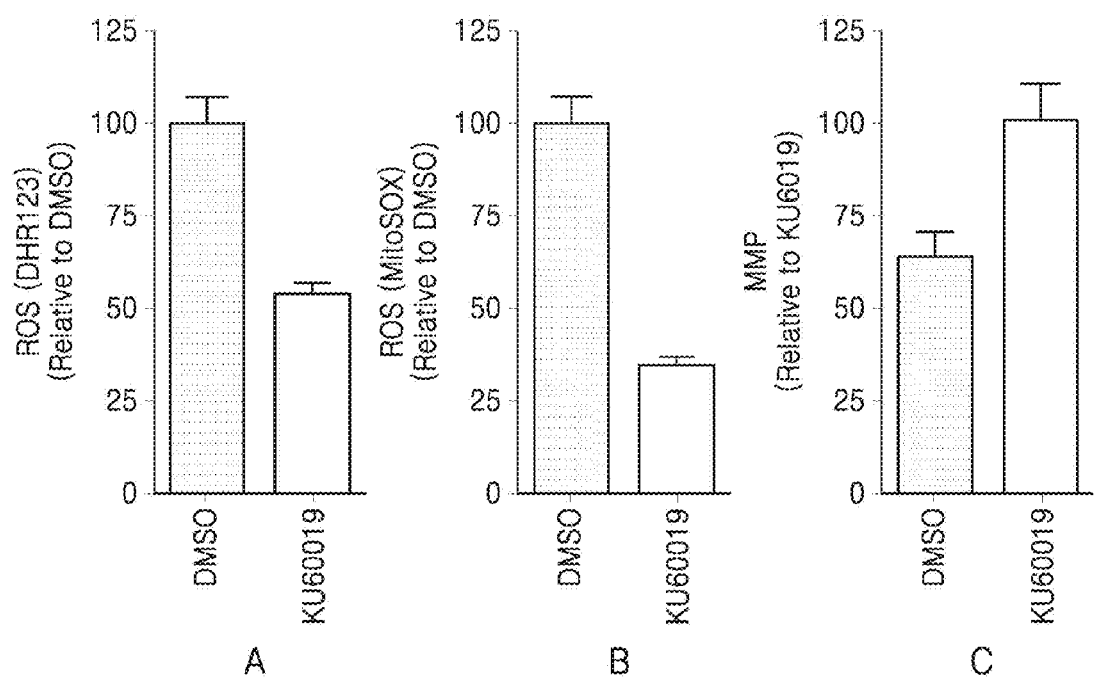
FIG. 8 is a series of graphs showing results of measuring a reactive oxygen species (ROS) concentrations (A and B) and a mitochondrial activity potential (C) of senescent cells that are cultured in the presence of KU-60019.

FIG. 8 is a graph showing results of measuring the ROS concentrations (A and B) and the mitochondrial activity potential (C) of the senescent cells that were cultured in the presence of KU-60019.

As shown in FIG. 8, the amount of ROS, as compared to a control, significantly decreased in the cells that were cultured in the presence of KU-60019.

FIG. 8A is a graph showing results of measuring DHR123 and FIG. 8B is a graph showing results of measuring MitoSOX. DHR123 is a dying reagent capable of measuring the ROS in various ways, and under these two conditions, the ROS was analyzed. In FIG. 8A, DHR123 refers to dihydrorhodamine as a positive control group with respect to the oxidant generation.

The mitochondrial activity potential (i.e., mitochondrial membrane potential) was measured according to the protocol of the manufacturer using the MitoProbe™ JC-1 assay kit for flow cytometry (Life technologies: T3168). JC-1 compound exhibits potential-dependent accumulation in mitochondria, indicated by a fluorescence emission shift from green (about 529 nm) to red (about 590 nm). Consequently, mitochondrial depolarization is indicated by a decrease in the red/green fluorescence intensity ratio. The cultured cells were analyzed by flow cytometry by using an FACSCaliber (Beckton Dickinson) using excitation at a wavelength of 488 nm, and band-pass emission light filters at a wavelength of 530/30 nm and 585/42 nm. The results were analyzed using Cell Quest 3.2 software (Beckton Dickinson). FIG. 8C is a graph showing results of measuring the mitochondrial membrane potential of the cells. As shown in FIG. 8C, the mitochondrial membrane potential of the cells, as compared to a control group, significantly increased in the cells that were cultured in the presence of KU-60019. In FIG. 8C, MMP on the vertical axis refers to the mitochondria membrane potential.

To determine the extent of recovery of the senescent cells to the DNA damage in accordance with the ATM-kinase inhibitor, a DNA comet assay (Trevigen, 4250-050-K) was carried out according to the protocol of the manufacturer. The principle of the DNA comet assay is based on gel electrophoresis. The damaged DNA moves farther away in the electrophoresis process than the undamaged DNA, resulting in the formation of a comet-tail shape. Afterwards, a slide used herein was stained with cyber green (SYBR Green), so that the tail length of the DNA fragment was measured by using fluorescence microscopy to confirm the extent of the DNA damage. The extent of the DNA damage may be measured as a tail moment value obtained by multiplying tail DNA % by the distance of migration of DNA fragmentation from the nucleus or the tail length.

Figure 9:
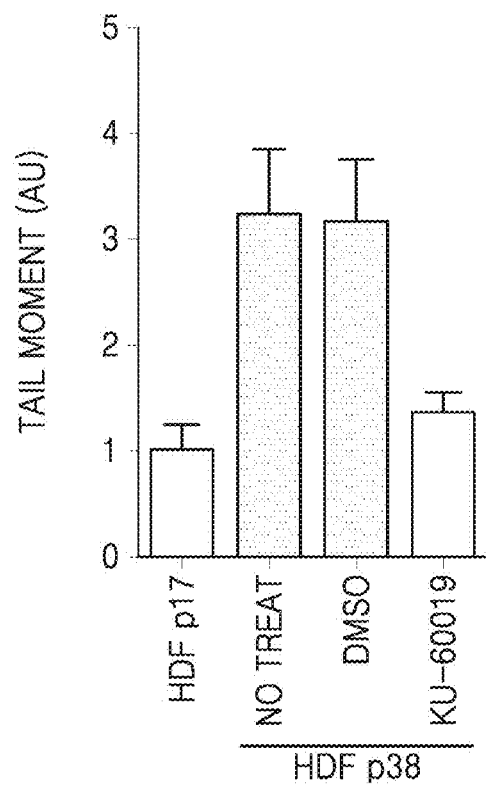
FIG. 9 is a graph showing results of measuring the extent of DNA damage in fibroblasts (passage 38) that are cultured in the presence of an ATM-kinase inhibitor KU-60019 (0.5 μM), by using a DNA comet assay.

FIG. 9 is a graph showing results of measuring the extent of DNA damage in the senescent fibroblasts (passage 38), which were cultured in the presence of an ATM-kinase inhibitor KU-60019 (0.5 µM), according to the DNA comet assay. In FIG. 9, the senescent human fibroblast cells (passage 38) were cultured in a medium containing KU-60019 (0.5 µM) in a $CO_2$ incubator at a temperature of 37° C. for 4 weeks. The medium was replaced by a fresh medium containing KU-60019 (0.5 µM), once every 4 days. In addition, as a negative control group, the cells were cultured under the same conditions as described above, except that a medium used herein was free from any treatment or contained DMSO (0.05 (v/v) %). As young cells, cells of passage 17, in which the cell doubling time was 2 to 3 days, were used. When culturing the cells of passage 17, KU-60019 was not added thereto. As shown in FIG. 9, the young cells had a short tail moment length. However, in the negative control group of the cells, the tail moment length was increased and the cells became senescent, resulting in increased DNA damage. In the DNA comet assay, the tail moment is defined as the product of the tail length and the fraction of total DNA in the tail, and that is, refers to a length of the tail shown on the gel electrophoresis. Thus, it is deemed that the shorter the tail length, the less DNA damage the cells had. However, the DNA-damage cells that were cultured in the presence of KU-60019, as compared to the control group (DMSO) were significantly recovered up to the young cellular levels. In FIG. 9, "HDF p17" and "HDF p38" respectively refer to "human dermal fibroblast passage 17" and "human dermal fibroblast passage 38".

(3) Influence of KU-60019 on Recovery of Early Senescent Cells

Progeria senescent fibroblasts (Hutchinson-Gilford Progeria Syndrome Skin Fibroblasts, Coriell Cell Repositories, AG03198 B) were inoculated into a DMEM medium containing 10% FBS, 100 units/ml of penicillin, and 100 µg/ml of streptomycin (wherein all antibiotics were purchased from Gibco-BRL, Grand Island, N.Y.), and then, cultured in a 5% $CO_2$ incubator at a temperature of 37° C. When progeria senescent cells were grown to about 85% confluency in a plate, the progeria senescent cells were subjected to subculture. The early subculture was carried out at a split ratio of 1:4, and the late subculture was carried out at a split ratio of 1:2. When the cell doubling time was 14 days, the cells were considered to be progeria senescent fibroblasts (passages 16 to 17).

The progeria senescent fibroblasts (passage 17) were inoculated into each well of a 6-well plate at a concentration of 2,000 cells/well, and then, cultured in a 5% $CO_2$ incubator at a temperature of 37° C. in the presence of an ATM-kinase inhibitor KU-60019 (0.5 µM). The medium was replaced by a fresh medium containing KU-60019 (0.5 µM), once every 4 days. In addition, as a negative control group, the cells were cultured under the same conditions as described above, except that a medium used herein contained DMSO (0.05 (v/v) %).

Figure 10:
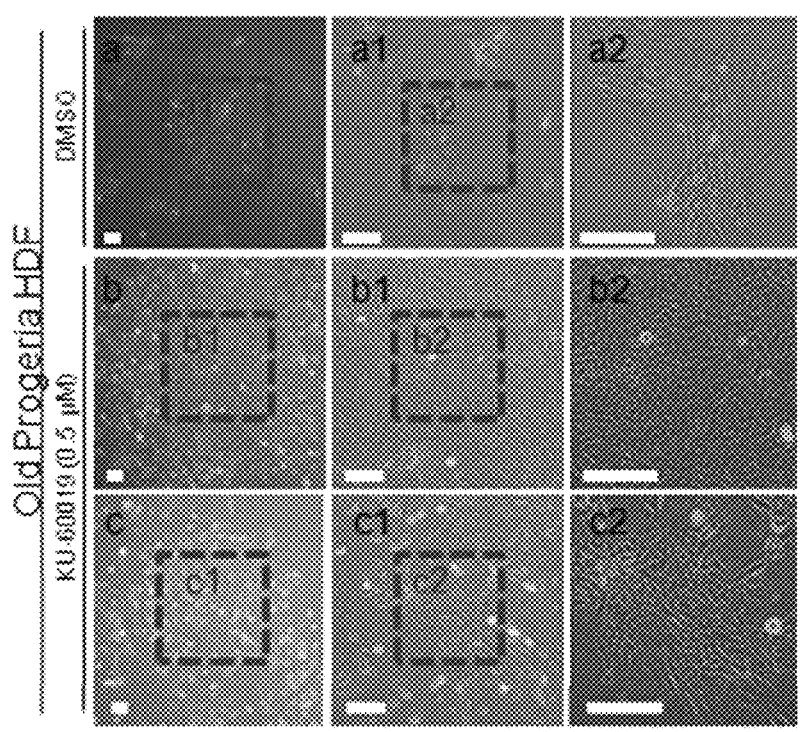
FIG. 10 is a view showing a morphological change of progeria senescent fibroblasts (passage 17) that are cultured in the presence of an ATM-kinase inhibitor KU-60019 (0.5 μM)

FIG. 10 is a view showing a morphological change of the progeria senescent fibroblasts (passage 17) that were cultured in the presence of an ATM-kinase inhibitor KU-60019 (0.5 µM). In FIG. 10, "Old Progeria HDF" refers to "a human dermal fibroblast (passage 17) separated from a progeria patient".

In FIG. 10, a human dermal fibroblast was cultured in the presence of the ATM-kinase inhibitor KU-60019 (0.5 µM), and then, the cell shapes were photographed using a microscope. To provide a better view of the cells formed in a dashed square a, a dashed square a1 was randomly selected, and then, the cells are shown enlarged in the dashed square a1. To provide a better view of the cells formed in the dashed square a1, a dashed square a2 was randomly selected, and then, the cells in the dashed square a2 are shown enlarged. As shown in FIG. 10, as compared with the control group (DMSO), the cells exist in a great number in the presence of KU-60019 and show a spindle form that is usually shown by young cells (at a scale bar 20 µm). The b and c images are captured from the same plate in different views.

Figure 11:
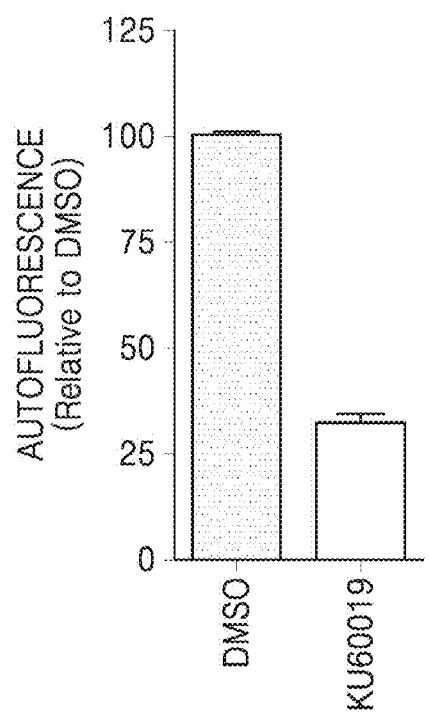
FIG. 11 is a graph showing lipofuscin measured in cells that are cultured in the presence of KU-60019.

In addition, the amounts of lipofuscin in the cells cultured as described above were measured. The progeria senescent fibroblasts (passage 17) that became senescent in the presence of KU-60019 (0.5 µM) were cultured in a $CO_2$ incubator at a temperature of 37° C. for 4 weeks. The medium was replaced by a fresh medium containing KU-60019 (0.5 µM), once every 4 days. Lipofuscin is characterized by having autofluorescence capability, and in this regard, the cultured cells were irradiated with a wavelength of 488 nm by using a FACSCaliber (Beckton Dickinson), and then, measured with radiation emitted from a wavelength of 520 nm. The results were analyzed using Cell Quest 3.2 software (Beckton Dickinson). FIG. 11 is a graph showing lipofuscin measured in the cells that were cultured in the presence of KU-60019. As shown in FIG. 11, the amount of lipofuscin, as compared to a control group, significantly decreased in the cells cultured in the presence of KU-60019.

In addition, the occurrence of mitochondrial damage in the cells was confirmed by using a well-known method measuring ROS and mitochondrial membrane potential.

Figure 12:
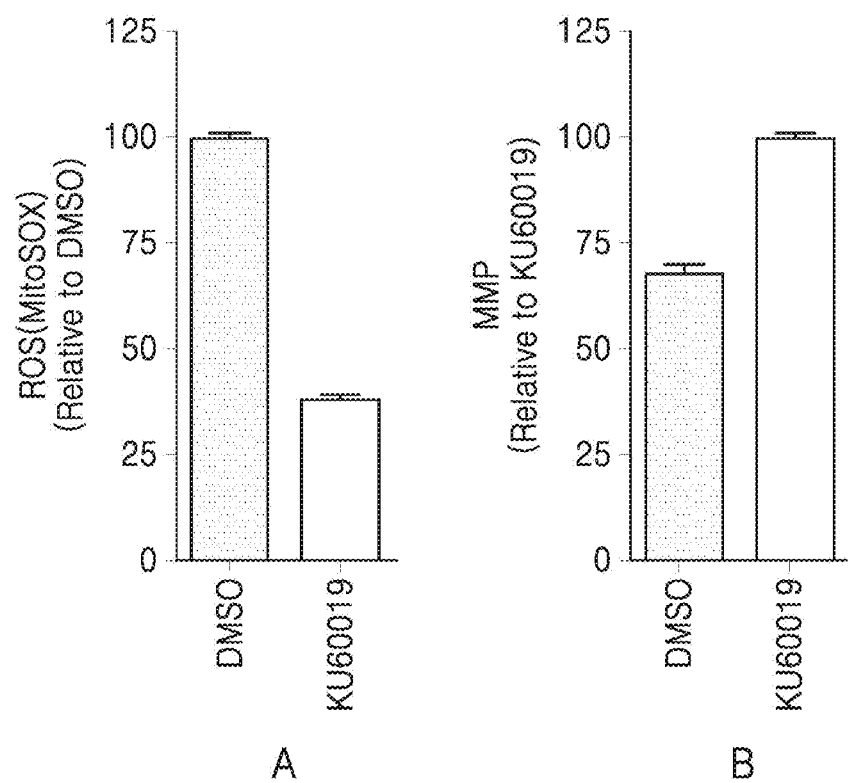
FIG. 12 is a series of graphs showing results of measuring ROS (A) and mitochondrial activity potential (B) of progeria senescent fibroblasts (passage 17) that are cultured in the presence of an ATM-kinase inhibitor KU-60019 (0.5 μM)

ROS was measured according to the protocol of the manufacturer using a 0.2 µM MitoSOX™ Red reagent (Invitrogen, M36008). In detail, 2 µL of the reagent that was stored in a 1,000-fold concentration was added to a 2 ml medium sufficiently enough to cover the cultured cells that were attached to a coverslip. While being protected from light, the cells were further incubated at a temperature of 37° C. for 30 minutes. The cultured cells were irradiated with a wavelength of 520 nm by using a FACSCaliber (Beckton Dickinson), and then, measured with radiation emitted from a wavelength of 580 nm. The results were analyzed using Cell Quest 3.2 software (Beckton Dickinson). FIG. 12 is a graph showing results of measuring ROS (A) and mitochondrial membrane potential (B) of the progeria senescent fibroblasts (passage 17) that were cultured in the presence of an ATM-kinase inhibitor KU-60019 (0.5 µM). As shown in FIG. 12A, as compared to the control group (DMSO) the amount of ROS significantly decreased in the cells that were cultured in the presence of KU-60019.

The mitochondrial activity potential (i.e., mitochondrial membrane potential) was measured according to the protocol of the manufacturer of the MitoProbe™ JC-1 assay kit for flow cytometry (Life technologies: T3168). JC-1 compound exhibits potential-dependent accumulation in mitochondria, indicated by a fluorescence emission shift from green (about 529 nm) to red (about 590 nm). Consequently, mitochondrial depolarization is indicated by a decrease in the red/green fluorescence intensity ratio. The cultured cells were analyzed by flow cytometry by using an FACSCaliber (Beckton Dickinson) using excitation at a wavelength of 488 nm, and band-pass emission light filters at a wavelength of 530/30 nm and 585/42 nm. The results were analyzed using Cell Quest 3.2 software (Beckton Dickinson). FIG. 12 is a graph showing results of measuring mitochondrial activity potential (B) of the cultured cells. As shown in FIG. 12B, the mitochondrial activity potential, as compared to a control group, significantly increased in the presence of KU-60019. Referring to FIGS. 12A and 12B, it was confirmed that the activity of the mitochondria increased in the presence of KU-60019.

To determine the extent of recovery of the senescent cells to the DNA damage in accordance with the ATM-kinase inhibitor, the DNA comet assay (Trevigen, 4250-050-K) was carried out according to the protocol of the manufacturer. The principle of the DNA comet assay is based on gel electrophoresis. The damaged DNA moves farther away in the electrophoresis process than the undamaged DNA, resulting in the formation of a comet-tail shape. Afterwards, a slide used herein was stained with cyber green (SYBR Green), so that the tail length of the DNA fragment was measured by using fluorescence microscopy to confirm the extent of the DNA damage. The extent of the DNA damage may be measured as a tail moment value obtained by multiplying tail DNA % by the distance of migration of DNA fragmentation from the nucleus or the tail length.

Figure 13:
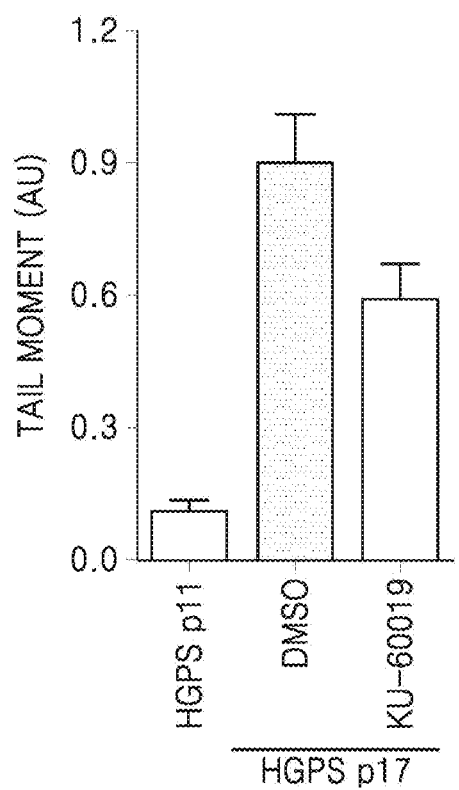
FIG. 13 is a graph showing results of measuring a DNA damage degree of progeria senescent fibroblasts (passage 17) that are cultured in the presence of an ATM-kinase inhibitor KU-60019 (0.5 μM), by using a DNA comet assay.

FIG. 13 is a graph showing results of measuring the extent of DNA damage in the progeria senescent fibroblasts (passage 17), which were cultured in the presence of an ATM-kinase inhibitor KU-60019 (0.5 µM), according to the DNA comet assay. In FIG. 13, the progeria senescent fibroblasts (passage 17) were cultured in a medium containing KU-60019 (0.5 µM) in a $CO_2$ incubator at a temperature of 37° C. for 4 weeks. The medium was replaced by a fresh medium containing KU-60019 (0.5 µM), once every 4 days. As young cells, cells (HGPS p11) of passage 11, in which the cell doubling time was 6 to 7 days, (HGPS p11) were used. In addition, in the preparation of negative control groups, a medium containing DMSO (0.05 (v/v) %) was used under the same conditions described above. As shown in FIG. 13, the young cells had a short tail moment length. However, in the negative control group of the senescent cells (DMSO-treated groups), the tail moment length was increased and the cells became senescent, resulting in increased DNA damage. However, as compared to the control group (DMSO), the DNA damage significantly decreased in the presence of KU-60019. In FIG. 13, "HGPS p11" and "HGPS p17" respectively refer to "Hutchinson-Gilford Progeria Syndrome Skin Fibroblasts passages 11 and 17".

In addition, the influence of the ATM-kinase inhibitor KU-60019 on the expression of SA-β-gal in the cells proliferated by the culture was confirmed by using a β-galactosidase staining kit (Cell Signaling Technology, #9860, Beverly, Mass.). According to the protocol of the manufacturer, a pH 6.0 X-gal chromogenic substrate was incubated overnight at a temperature of 37° C. to stain the cells having immobilized cell growth.

Figure 14:
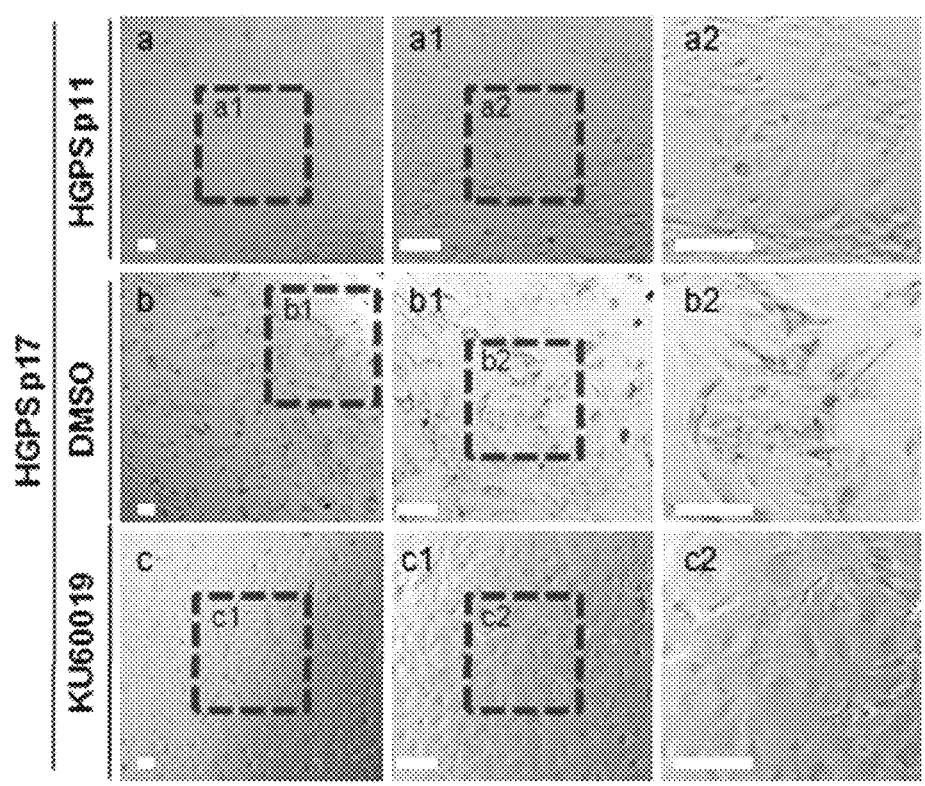
FIG. 14 is a view showing activity of SA-β-galactosidase of cells that are cultured in the presence of KU-60019 (0.5 μM)
Figure 15:
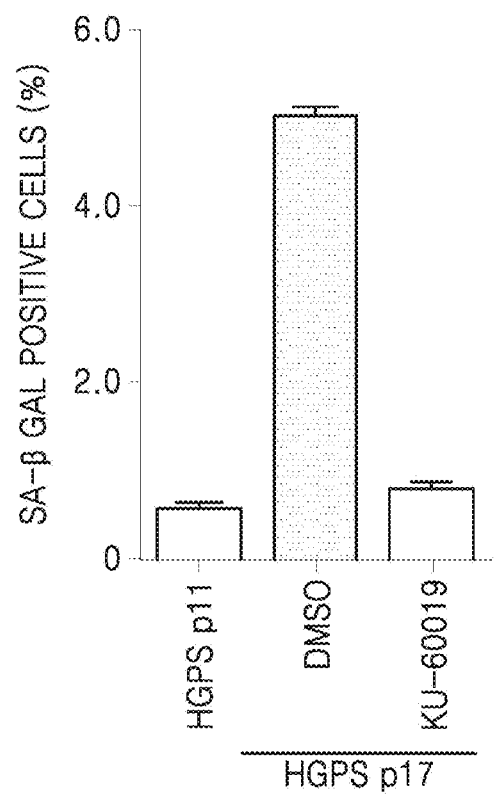
FIG. 15 is a graph showing a percentage of the cells of FIG. 14 having the activity of SA-β-galactosidase.

FIGS. 14 and 15 respectively are a view showing SA-β-gal activity of the cells that were cultured in the presence of KU-60019 (0.5 µM) (FIG. 14) and a graph showing a percentage of the cells having the SA-β-gal activity (FIG. 15). Referring to FIGS. 14 and 15, KU-60019 (0.5 µM) was added to a medium for culturing the progeria senescent fibroblasts (passage 17), and then, the cells were cultured in a $CO_2$ incubator at a temperature of 37° C. for 4 weeks. The medium was replaced by a fresh medium containing KU-60019 (0.5 µM), once every 4 days. As young cells, cells of passage 11, in which the cell doubling time was 6 to 7 days, were used. When culturing HPGS p11, KU-60019 was not added thereto. In addition, in the preparation of a negative control group, a medium containing DMSO (0.05 (v/v) %) was used under the same conditions described above. To provide a better view of the stained cells shown in the image a, a dashed square a1 was randomly selected, and then, the stained cells in the dashed square a1 are shown enlarged. To provide a better view of the stained cells shown in the dashed square a1, a dashed square a2 was randomly selected, and then, the stained cells in the dashed square a2 are shown enlarged (at a scale bar 20 µm). The same procedure applies similarly to the images b and c.

As shown in FIGS. 14 and 15, the number of cells that express β-galactosidase was very small in the young cells. However, number of cells that express β-galactosidase significantly increased in the negative control group (DMSO-treated group) of the senescent cells. That is, it was confirmed that the number of cells that express β-galactosidase, as compared to the control group (DMSO-treated group), significantly decreased in the presence of the compound, KU-60019.

(4) Influence of KU-60019 on Recovery of Senescent Myoblast

A human myoblast cell line (Human Skeletal Muscle Myoblasts, Lonza CC-2580 LOT:0000387550) was inoculated into a plate (Greiner Bio One, 658950), which was coated with Collagen Type I, by using an SkBM™-2 Basal Medium (Lonza CC-3246) containing SkGM™-2 Single-Quots™ Kit (Lonza CC-3244), and then, cultured in a 5%

CO₂ incubator at a temperature of 37° C. When the cells were grown to about 85% confluency in the plate, the cells were subjected to subculture. The early subculture was carried out at a split ratio of 1:4, and the late subculture was carried out at a split ratio of 1:2. When the cell doubling time was 14 days, the cells were considered to be senescent fibroblasts (passages 10 to 12).

The senescent cells were inoculated into each well of a Collagen Type I-coated 6-well plate (Greiner Bio One, 657950) at a concentration of 2,000 cells/well, and then, the senescent myoblasts (passage 11) were cultured in a medium containing an ATM-kinase inhibitor KU-60019 (0.5 µM) in a CO₂ incubator at a temperature of 37° C. for 4 weeks. The medium was replaced by a fresh medium containing KU-60019 (0.5 µM), once every 4 days. In addition, as a negative control group, the cells were cultured under the same conditions as described above, except that a medium used herein contained DMSO (0.05 (v/v) %).

Figure 16:
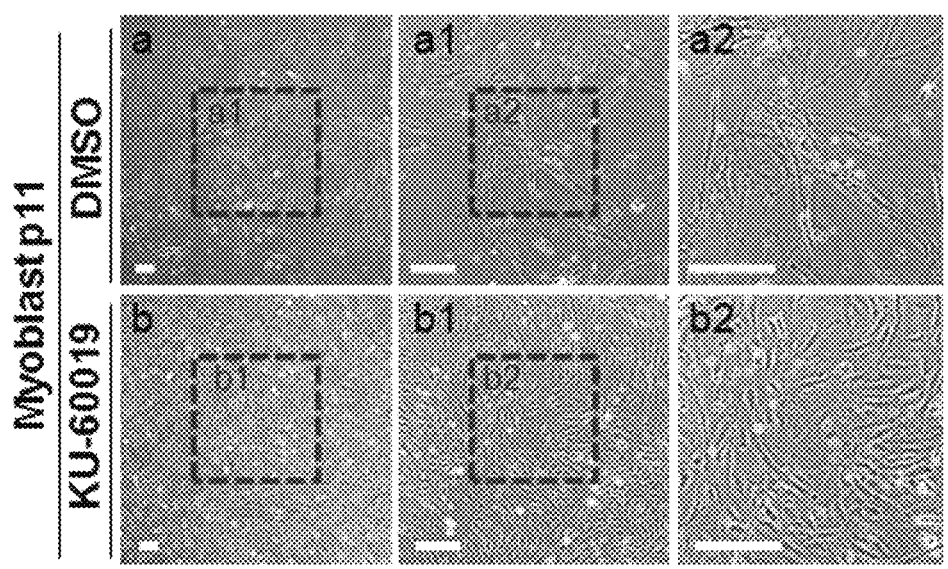
FIG. 16 is a view showing a morphological change of myoblasts (passage 11) that are cultured in the presence of an ATM-kinase inhibitor KU-60019 (0.5 μM)

FIG. 16 is a view showing a morphological change of myoblasts (passage 11) that were cultured in the presence of an ATM-kinase inhibitor KU-60019 (0.5 µM).

In FIG. 16, the myoblasts were cultured in the presence of the ATM-kinase inhibitor KU-60019 (0.5 µM), and then, the cell shapes were photographed using a microscope. To provide a better view of the cells formed in a dashed square a, a dashed square a1 was randomly selected, and then, the cells in the dashed square a1 are shown enlarged. To provide a better view of the cells formed in the dashed square a1, a dashed square a2 was randomly selected, and then, the cells in the dashed square a2 are shown enlarged. The same procedure applies similarly to the image b. As shown in FIG. 16, as compared with the control group (DMSO), the cells exist in a great number in the presence of KU-60019 and show a spindle form that is usually shown by young cells (at a scale bar 20 µm).

Figure 17:
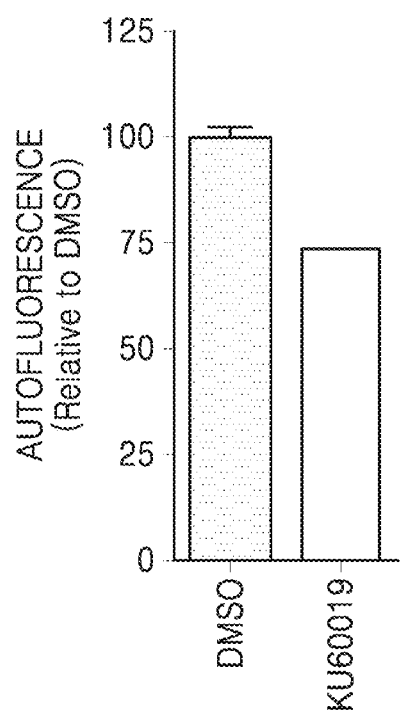
FIG. 17 is a graph showing measured lipofuscin of cells that are cultured in the presence of KU-60019.

In addition, the amounts of lipofuscin in the cells cultured as described above were measured. The senescent myoblast (passage 11) that became senescent in the presence of KU-60019 (0.5 µM) were cultured in a CO₂ incubator at a temperature of 37° C. for 4 weeks. The medium was replaced by a fresh medium containing KU-60019 (0.5 µM), once every 4 days. Lipofuscin is characterized by having autofluorescence capability, and in this regard, the cultured cells were irradiated with a wavelength of 488 nm by using a FACSCaliber (Beckton Dickinson), and then, measured with radiation emitted from a wavelength of 520 nm. The results were analyzed using Cell Quest 3.2 software (Beckton Dickinson). FIG. 17 is a graph showing lipofuscin measured in the cells that were cultured in the presence of KU-60019. As shown in FIG. 17, the amount of lipofuscin, as compared to a control group (DMSO), significantly decreased in the cells cultured in the presence of KU-60019.

In addition, the occurrence of mitochondrial damage in the cells was confirmed by using a well-known method measuring ROS and mitochondrial membrane potential.

ROS was measured according to the protocol of the manufacturer using a 0.2 µM MitoSOX™ Red reagent (Invitrogen, M36008). In detail, 2 µL of the reagent that was stored in a 1,000-fold concentration was added to a 2 ml medium sufficiently enough to cover the cultured cells that were attached to a coverslip. While being protected from light, the cells were further incubated at a temperature of 37° C. for 30 minutes. The cultured cells were irradiated with a wavelength of 520 nm by using a FACSCaliber (Beckton Dickinson), and then, measured with radiation emitted from a wavelength of 580 nm. The results were analyzed using Cell Quest 3.2 software (Beckton Dickinson).

Figure 18:
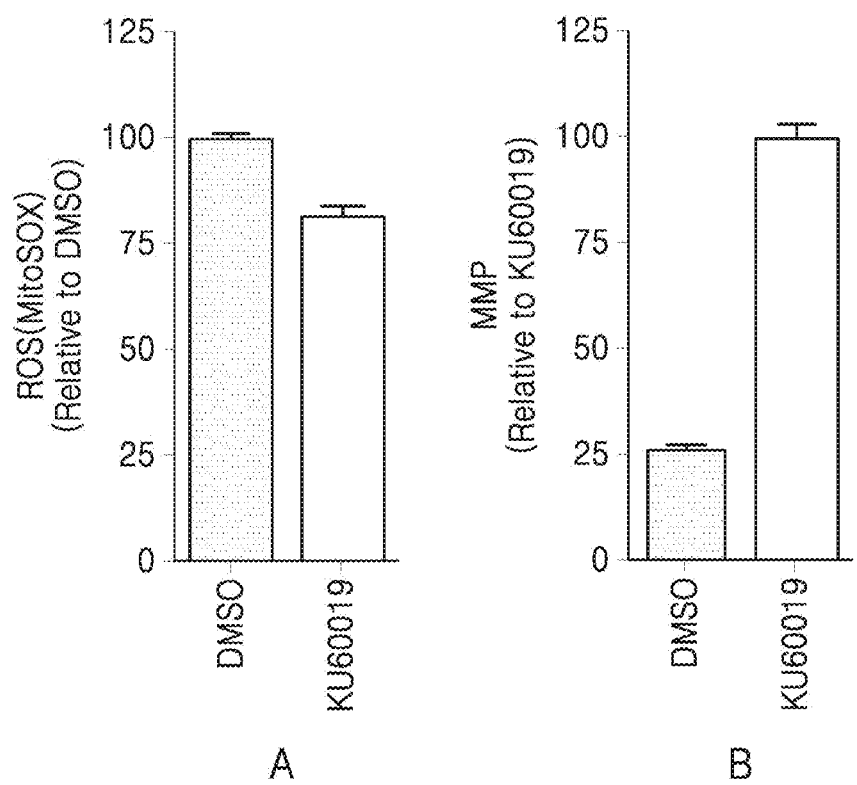
FIG. 18 is a graph showing results of measuring a ROS (A) and a mitochondrial activity potential (B) of myoblasts (passage 11) that are cultured in the presence of an ATM-kinase inhibitor KU-60019 (0.5 μM)

FIG. 18 is a graph showing results of measuring ROS (A) and mitochondrial activity potential (B) of the myoblast (passage 11) that were cultured in the presence of an ATM-kinase inhibitor KU-60019 (0.5 µM). As shown in FIG. 18A, as compared with the control group (DMSO), the amount of ROS significantly decreased in the cells that were cultured in the presence of KU-60019, and that is, the amount of superoxide significantly decreased.

The mitochondrial activity potential (i.e., mitochondrial membrane potential) was measured according to the protocol of the manufacturer using the MitoProbe™ JC-1 assay kit for flow cytometry (Life technologies: T3168). JC-1 compound exhibits potential-dependent accumulation in mitochondria, indicated by a fluorescence emission shift from green (about 529 nm) to red (about 590 nm). Consequently, mitochondrial depolarization is indicated by a decrease in the red/green fluorescence intensity ratio. The cultured cells were analyzed by flow cytometry by using an FACSCaliber (Beckton Dickinson) using excitation at a wavelength of 488 nm, and band-pass emission light filters at a wavelength of 530/30 nm and 585/42 nm. The results were analyzed using Cell Quest 3.2 software (Beckton Dickinson).

FIG. 18B is a graph showing results of measuring mitochondrial activity potential of the cultured myoblasts. As shown in 18B, the mitochondrial activity potential, as compared to a control group, significantly increased in the presence of KU-60019. Referring to FIGS. 18A and 18B, the mitochondrial activity potential, as compared to a control group, significantly increased in the presence of KU-60019.

(5) Influence of KU-60019 on Metabolic Activity Recovery of Senescent Fibroblast (Passage 37)

A human fibroblast cell line was inoculated into DMEM containing 10% FBS, 100 units/ml of penicillin, and 100 µg/ml of streptomycin (wherein these two antibiotics were purchased from Gibro-BRL, Grand Island, N.Y.), and then, cultured in a 5% CO₂ incubator at a temperature of 37° C. The fibroblast cell line (i.e., M11 strain) was a cell line derived from the foreskin of an 11-year-old boy. When the cells were grown to about 85% confluency in a plate, the cells were subjected to subculture. The early subculture was carried out at a split ratio of 1:4, and the late subculture was carried out at a split ratio of 1:2. When the cell doubling time was 14 days, the cells were considered to be senescent fibroblasts (passages 35 to 37).

The medium containing 0.5 µM of an ATM-kinase inhibitor KU-60019 (SELLECKCHEM, S1570, salt) was added to the wells, and the senescent fibroblasts (passage 37) were inoculated into each well of the 6-well plate at a concentration of 2,000 cells/well, and then, KU-60019 was added to each well of the 6-well plate. In addition, as a negative control group, the cells were cultured under the same conditions as described above, except that a medium used herein contained DMSO (0.05 (v/v) %). As young cells, cells of passage 11 (HDF p16), in which the cell doubling time was 2 to 3 days, were used.

Figure 19:
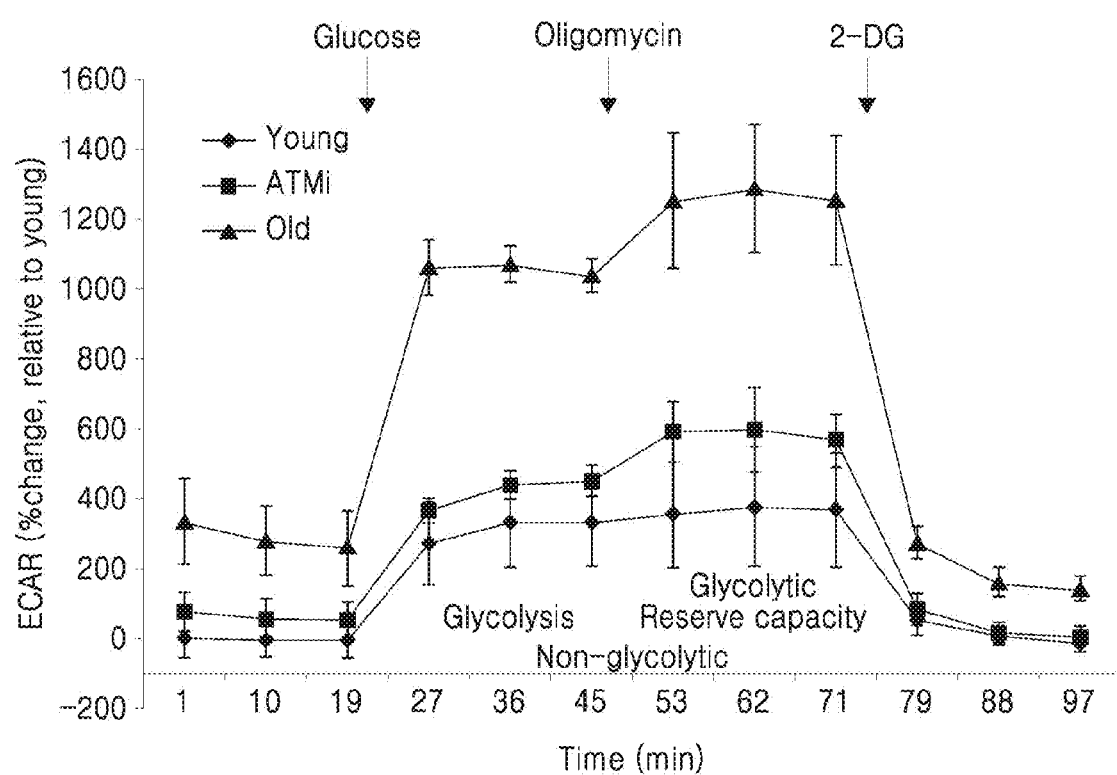
FIG. 19 is a graph showing experimental results for the recovery of cell metabolism in cells that become senescent in the presence of an ATM-kinase inhibitor KU-60019.

FIG. 19 is a graph of measuring extracellular acidification rates (ECARs) of young cells, senescent cells, and ATM-kinase inhibitor (ATMi)-treated cells, by using an XFe24 flux analyzer (Seahorse Bioscience). The XFe24 flux analyzer and a Prep Station (Seahorse Bioscience XFe24 Instrument, Billerica, Mass., USA) were used according to the protocol of the manufacturer. Briefly, 50,000 cells were distributed to each well of an XFe24 cell-culture plate of the XF24 FluxPak (Seahorse Bioscience, Part#100850-001), and then, cultured in a 5% $CO_2$ incubator at a temperature of 37° C. for 16 hours. Afterwards, the medium was replaced by an XF Assay medium (Seahorse Bioscience, Part#102365-100) that does not include glucose, and then, the cells were cultured for another hour in the same incubator. The XFe24 flux analyzer was used to measure a basal ECAR during an incubation time between 1 and 19 minutes, and then, the cells were treated with glucose to have a final concentration of 10 mM (XF Glycolysis Stress Test kit, Part#102194-100) for glycolysis during an incubation time between 27 and 45 minutes. The XFe24 flux analyzer was used to measure an ECAR that was increased by glycolysis. The cells were treated with oligomycin (XF Glycolysis Stress Test kit, Part#102194-100), which inhibits ATP synthesis by mitochondria, to have a final concentration of 1 μM during an incubation time between 53 and 71 minutes. Glycolysis was allowed to be generated at a maximum, and the XFe24 flux analyzer was used to measure an ECAR. To stop intracellular glycolysis during an incubation time between 79 and 97 minutes, the cells were treated with 2-Dexoy-D-glucose (2-DG) (XF Glycolysis Stress Test kit, Part#102194-100) to have a final concentration of 100 mM, and then, the XFe24 flux analyzer was used to measure a non-glycolytic ECAR. The measured ECAR was corrected to a cell number ratio.

Figure 20:
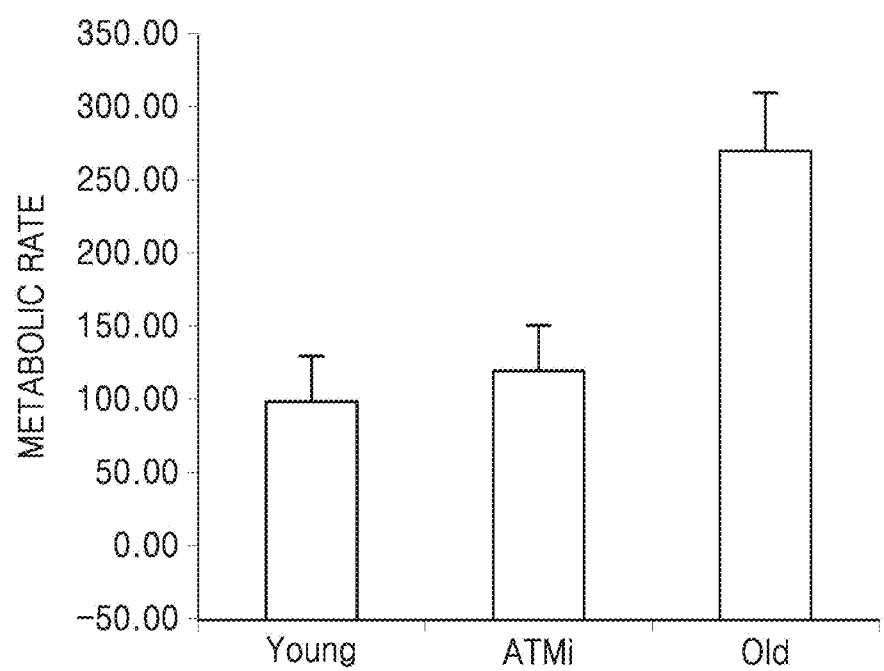
FIG. 20 is a graph showing metabolic rates of non-glycolysis in cells that become senescent in the presence of an ATM-kinase inhibitor KU-60019.

FIG. 20 is a graph showing metabolic rates of non-glycolysis in young cells, cells recovered from senescence by KU-60019 (i.e., ATMi-treated cells), and old cells. In FIG. 20, the vertical axis refers to metabolic rates of non-glycolysis compared among cells treated with an ATM-kinase inhibitor KU-60019 (i.e., ATMi-treated cells), young cells, and old cells. Then, it was confirmed that the treatment with KU-060019 resulted in a similar metabolic rate of non-glycolysis with that of the young cells.

(6) Influence of CP-466722 on Senescent Cells (6.1) Influence on Proliferation of Human Senescent Dermal Fibroblast A human fibroblast cell line was inoculated into DMEM containing 10% FBS, 100 units/ml of penicillin, and 100 μg/ml of streptomycin (wherein these two antibiotics were purchased from Gibro-BRL, Grand Island, N.Y.), and then, cultured in a 5% $CO_2$ incubator at a temperature of 37° C. The fibroblast cell line (i.e., M11 strain) was a cell line derived from the foreskin of an 11-year-old boy. When the cells were grown to about 85% confluency in a plate, the cells were subjected to subculture. The early subculture was carried out at a split ratio of 1:4, and the late subculture was carried out at a split ratio of 1:2. When the cell doubling time was 14 days, the cells were considered to be senescent fibroblasts (passages 35 to 37).

The senescent fibroblasts (passage 37) were inoculated into each well of a 6-well plate containing a 0.1 μM ATM-kinase inhibitor CP-466722 (SELLECKCHEM, S2245, salt), at a concentration of 2,000 cells/well, and then, CP-466722 was added to each well of the 6-well plate at a concentration of 0.1 μM. In addition, as a negative control group, the cells were cultured under the same conditions as described above, except that a medium used herein contained DMSO (0.05 (v/v) %). The medium was replaced by a fresh medium containing CP-466722, once every 4 days, and then, CP-466722 was added thereto. After a lapse of 4 days, colonies formed on the medium were stained with 0.05% crystal violet dye.

Figure 21:
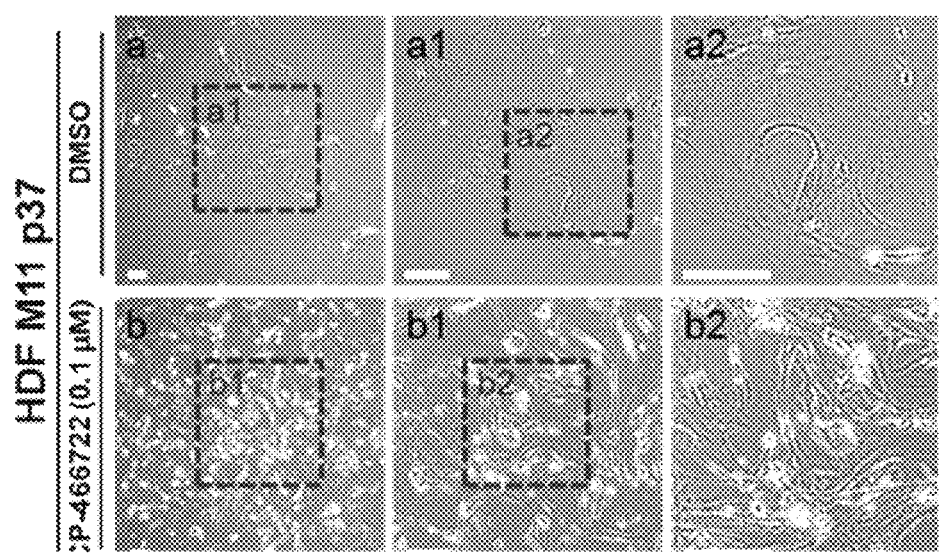
FIG. 21 is a view showing experimental results that confirm cell proliferation and formation of cell colonies in the presence of an ATM-kinase inhibitor, CP-466722.

FIG. 21 is a view showing experimental results that confirm cell proliferation and formation of cell colonies according to concentrations of the ATM-kinase inhibitor CP-466722.

As shown in FIG. 21, CP-466722 produced best results in the cell proliferation and the formation of cell colonies at concentration of 0.1 μM.

(6.2) Influence of CP-466722 on Recovery of Senescent Myoblast

A human myoblast cell line (Human Skeletal Muscle Myoblasts, Lonza CC-2580 LOT:0000387550) was inoculated into a plate (Greiner Bio One, 658950), which was coated with Collagen Type I, by using an SkBM™-2 Basal Medium (Lonza CC-3246) containing SkGM™-2 Single-Quots™ Kit (Lonza CC-3244), and then, cultured in a 5% $CO_2$ incubator at a temperature of 37° C. When the cells were grown to about 85% confluency in the plate, the cells were subjected to subculture. The early subculture was carried out at a split ratio of 1:4, and the late subculture was carried out at a split ratio of 1:2. When the cell doubling time was 14 days, the cells were considered to be senescent fibroblasts (passages 10 to 12)

The senescent cells were inoculated into each well of the Collagen Type I-coated 6-well plate (Greiner Bio One, 657950) at a concentration of 2,000 cells/well, and then, the senescent myoblasts (passage 11) were cultured in a medium containing an ATM-kinase inhibitor CP-466722 (0.1 μM) in a $CO_2$ incubator at a temperature of 37° C. for 4 weeks. The medium was replaced by a fresh medium containing CP-466722 (0.5 μM), once every 4 days. In addition, as a negative control group, the cells were cultured under the same conditions as described above, except that a medium used herein contained DMSO (0.05 (v/v) %).

Figure 22:
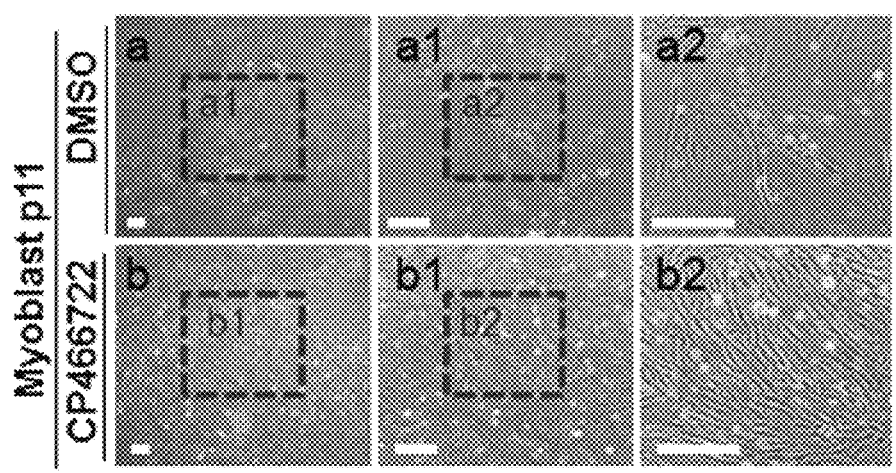
FIG. 22 is a view showing a morphological change of myoblasts (passage 11) that are cultured in the presence of an ATM-kinase inhibitor, CP-466722 (0.1 μM)

FIG. 22 is a view showing a morphological change of myoblasts (passage 11) that were cultured in the presence of an ATM-kinase inhibitor CP-466722 (0.1 μM).

In FIG. 22, the myoblasts were cultured in the presence of the ATM-kinase inhibitor CP-466722 (0.1 μM) and then, the cell shapes were photographed using a microscope. To provide a better view of the cells formed in a dashed square a, a dashed square a1 was randomly selected, and then, the cells in the dashed square a1 are shown enlarged. To provide a better view of the cells formed in the dashed square a1, a dashed square a2 was randomly selected, and then, the cells in the dashed square a2 are shown enlarged. The same procedure applies similarly to the image b. As shown in FIG. 22, as compared with the control group (DMSO), the cells exist in a great number in the presence of CP-466722 and show a spindle form that is usually shown by young cells (at a scale bar 20 μm).

Figure 23:
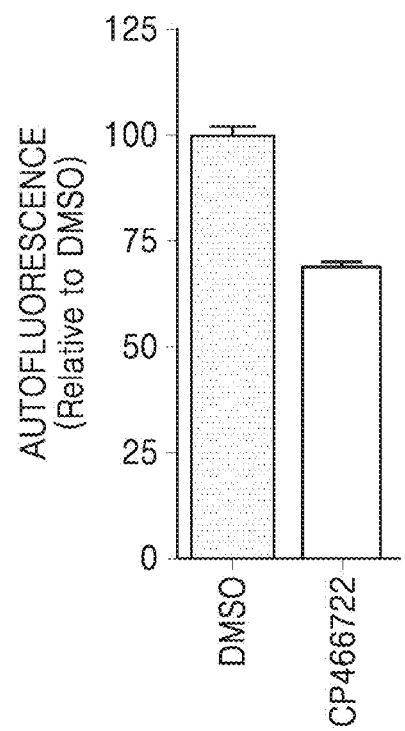
FIG. 23 is a graph showing measured lipofuscin of cells that are cultured in the presence of CP-466722.

In addition, the amounts of lipofuscin in the cells cultured as described above were measured. The senescent myoblast (passage 11) that became senescent in the presence of CP-466722 (0.1 μM) were cultured in a $CO_2$ incubator at a temperature of 37° C. for 4 weeks. The medium was replaced by a fresh medium containing CP-466722 (0.1 μM), once every 4 days. Lipofuscin is characterized by having autofluorescence capability, and in this regard, the cultured cells were irradiated with a wavelength of 488 nm by using a FACSCaliber (Beckton Dickinson), and then, measured with radiation emitted from a wavelength of 520 nm. The results were analyzed using Cell Quest 3.2 software (Beckton Dickinson). FIG. 23 is a graph showing lipofuscin measured in the cells that were cultured in the presence of CP-466722. As shown in FIG. 23, the amount of lipofuscin, as compared to a control group, significantly decreased in the cells cultured in the presence of CP-466722.

In addition, the occurrence of mitochondrial damage in the cells was confirmed by using a well-known method measuring ROS and mitochondrial membrane potential.

ROS was measured according to the protocol of the manufacturer using a 0.2 µM MitoSOX™ Red reagent (Invitrogen, M36008). In detail, 2 µL of the reagent that was stored in a 1,000-fold concentration was added to a 2 ml medium sufficiently enough to cover the cultured cells that were attached to a coverslip. While being protected from light, the cells were further incubated at a temperature of 37° C. for 30 minutes. The cultured cells were irradiated with a wavelength of 520 nm by using an FACSCaliber (Beckton Dickinson), and then, measured with radiation emitted from a wavelength of 580 nm. The results were analyzed using Cell Quest 3.2 software (Beckton Dickinson).

Figure 24:
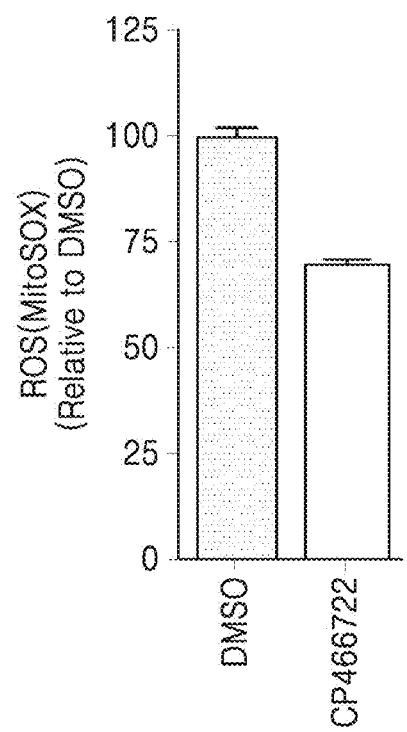
FIG. 24 is a graph showing measured ROS of myoblasts (passage 11) at are cultured in the presence of an ATM-kinase inhibitor, CP-466722 (0.1 μM)

FIG. 24 is a graph showing results of measuring ROS (A) and mitochondrial activity potential (B) of the myoblast (passage 11) that were cultured in the presence of an ATM-kinase inhibitor CP-466722 (0.1 µM). As shown in FIG. 24, as compared with the control group, the amount of ROS, as compared to a control group, significantly decreased in the cells that were cultured in the presence of CP-466722, and that is, the amount of superoxide significantly decreased.

(6.3) Influence of KU-466722 on Recovery of Early Senescent Fibroblast

Progeria senescent fibroblasts (Hutchinson-Gilford Progeria Syndrome Skin Fibroblasts, Coriell Cell Repositories, AG03198 B) were inoculated into a DMEM medium containing 10% FBS, 100 units/ml of penicillin, and 100 µg/ml of streptomycin (wherein all antibiotics were purchased from Gibco-BRL, Grand Island, N.Y.), and then, cultured in a 5% $CO_2$ incubator at a temperature of 37° C. When progeria fibroblast cells were grown to about 85% confluency in a plate, the progeria fibroblast cells were subjected to subculture. The early subculture was carried out at a split ratio of 1:4, and the late subculture was carried out at a split ratio of 1:2. When the cell doubling time was 14 days, the cells were considered to be progeria senescent fibroblasts (passages 16 to 17).

The progeria senescent fibroblasts (passage 17) were inoculated into each well of a 6-well plate at a concentration of 2,000 cells/well, and then, cultured in a 5% $CO_2$ incubator at a temperature of 37° C. in the presence of an ATM-kinase inhibitor CP-466722 (0.1 µM). The medium was replaced by a fresh medium containing CP-466722 (0.1 µM), once every 4 days. In addition, as a negative control group, the cells were cultured under the same conditions as described above, except that a medium used herein contained DMSO (0.05 (v/v) %).

Figure 25:
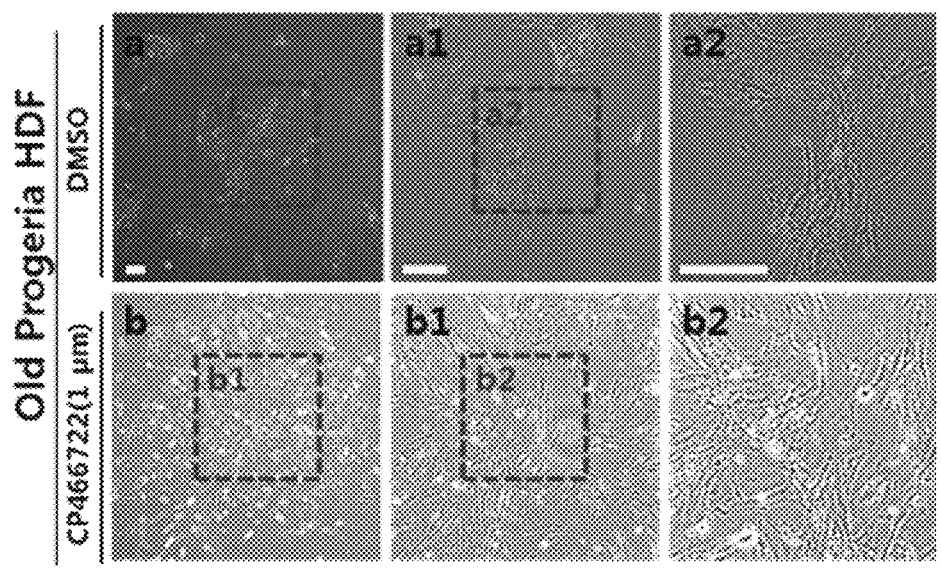
FIG. 25 is a view showing a morphological change of progeria senescent fibroblasts (passage 17) that are cultured in the presence of an ATM-kinase inhibitor, CP-466722 (0.1 µM)

FIG. 25 is a view showing a morphological change of the progeria senescent fibroblasts (passage 17) that were cultured in the presence of an ATM-kinase inhibitor CP-466722 (0.1 µM). In FIG. 25, "Old Progeria HDF" refers to "a human dermal fibroblast (passage 17) separated from a progeria patient".

In FIG. 25, the human dermal fibroblast was cultured in the presence of an ATM-kinase inhibitor CP-466722 (0.1 µM), and then, the cell shapes were photographed using a microscope. To provide a better view of the cells formed in a dashed square a, a dashed square a1 was randomly selected, and then, the cells n the dashed square a1 are shown enlarged. To provide a better view of the cells formed in the dashed square a1, a dashed square a2 was randomly selected, and then, the cells in the dashed square a2 are shown enlarged. As shown in FIG. 25, as compared with the control group (DMSO), the cells exist in a great number in the presence of CP-466722 and show a spindle form that is usually shown by young cells (at a scale bar 20 µm).

In addition, the amounts of lipofuscin in the cells cultured as described above were measured. The progeria senescent fibroblasts (passage 17) that became senescent in the presence of CP-466722 (0.1 µM) were cultured in a $CO_2$ incubator at a temperature of 37° C. for 4 weeks. The medium was replaced by a fresh medium containing CP-466722 (0.1 µM), once every 4 days. Lipofuscin is characterized by having autofluorescence capability, and in this regard, the cultured cells were irradiated with a wavelength of 488 nm by using a FACSCaliber (Beckton Dickinson), and then, measured with radiation emitted from a wavelength of 520 nm. The results were analyzed using Cell Quest 3.2 software (Beckton Dickinson). As a result, the amount of lipofuscin, as compared to a control group, significantly decreased in the cells cultured in the presence of CP-466722.

In addition, the occurrence of mitochondrial damage in the cells was confirmed by using a well-known method measuring ROS and mitochondrial membrane potential.

ROS was measured according to the protocol of the manufacturer using a 0.2 µM MitoSOX™ Red reagent (Invitrogen, M36008). In detail, 2 µL of the reagent that was stored in a 1,000-fold concentration was added to a 2 ml medium sufficiently enough to cover the cultured cells that were attached to a coverslip. While being protected from light, the cells were further incubated at a temperature of 37° C. for 30 minutes. The cultured cells were irradiated with a wavelength of 520 nm by using a FACSCaliber (Beckton Dickinson), and then, measured with radiation emitted from a wavelength of 580 nm. The results were analyzed using Cell Quest 3.2 software (Beckton Dickinson). As a result, as compared with the control group, the amount of ROS, as compared to a control group, significantly decreased in the cells that were cultured in the presence of CP-466722.

The mitochondrial activity potential (i.e., mitochondrial membrane potential) was measured according to the protocol of the manufacturer using the MitoProbe™ JC-1 assay kit for flow cytometry (Life technologies: T3168). JC-1 compound exhibits potential-dependent accumulation in mitochondria, indicated by a fluorescence emission shift from green (about 529 nm) to red (about 590 nm). Consequently, mitochondrial depolarization is indicated by a decrease in the red/green fluorescence intensity ratio. The cultured cells were analyzed by flow cytometry by using an FACSCaliber (Beckton Dickinson) using excitation at a wavelength of 488 nm, and band-pass emission light filters at a wavelength of 530/30 nm and 585/42 nm. The results were analyzed using Cell Quest 3.2 software (Beckton Dickinson).

Figure 26:
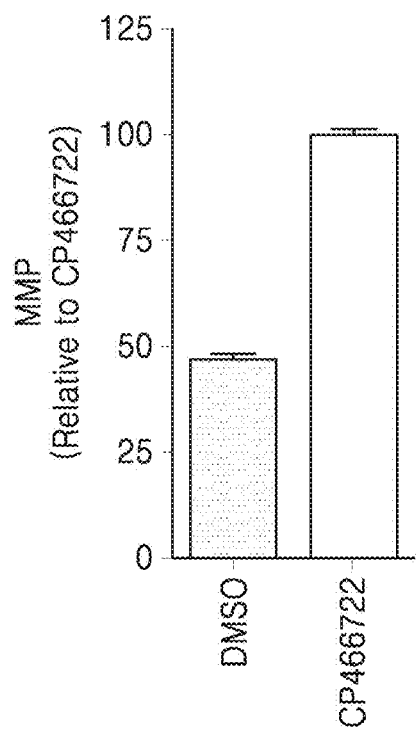
FIG. 26 is a graph showing a mitochondrial activity potential of progeria senescent fibroblasts (passage 17) that are cultured in the presence of an ATM-kinase inhibitor, CP-466722 (0.1 µM)

FIG. 26 a graph showing results of measuring mitochondrial activity potential of the progeria senescent fibroblasts (passage 17) that were cultured in the presence of an ATM-kinase inhibitor CP-466722 (0.1 µM). As shown in FIG. 26, the mitochondrial activity potential, as compared to a control group, significantly increased in the presence of CP-466722. Referring to FIG. 26, it was confirmed that the activity of the mitochondria increased in the presence of CP-466722.

To determine the extent of recovery of the senescent cells to the DNA damage in accordance with the ATM-kinase inhibitor, the DNA comet assay (Trevigen, 4250-050-K) was carried out according to the protocol of the manufacturer. The principle of the DNA comet assay is based on gel electrophoresis. The damaged DNA moves farther away in the electrophoresis process than the undamaged DNA, resulting in the formation of a comet-tail shape. Afterwards, a slide used herein was stained with cyber green (SYBR Green), so that the tail length of the DAN fragment was measured by using fluorescence microscopy to confirm the extent of the DNA damage. The extent of the DNA damage may be measured as a tail moment value obtained by multiplying tail DNA % by the distance of migration of DNA fragmentation from the nucleus or the tail length.

Figure 27:
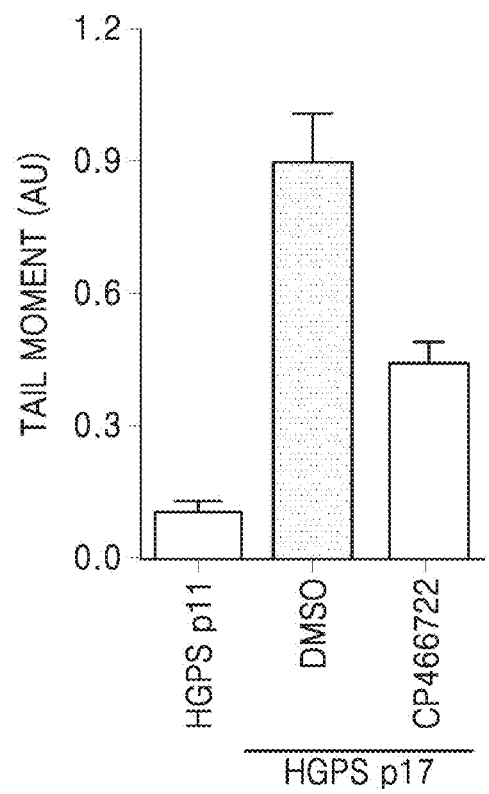
FIG. 27 is a graph showing results of measuring a DNA damage degree of progeria senescent fibroblasts (passage 17) that are cultured in the presence of an ATM-kinase inhibitor, CP-466722 (0.1 µM), by using a DNA comet assay.

FIG. 27 is a graph showing results of measuring the extent of DNA damage in the progeria senescent fibroblasts (passage 17), which were cultured in the presence of an ATM-kinase inhibitor CP-466722 (0.1 μM). In FIG. 27, the progeria senescent fibroblasts (passage 17) were cultured in a medium containing CP-466722 (0.1 μM) in a $CO_2$ incubator at a temperature of 37° C. for 4 weeks. The medium was replaced by a fresh medium containing CP-466722 (0.1 μM), once every 4 days. As young cells, cells (HGPS p11) of passage 11, in which the cell doubling time was 6 to 7 days (HGPS p11), were used. In addition, in the preparation of negative control groups, a medium containing DMSO (0.05 (v/v) %) was used under the same conditions described above. As shown in FIG. 27, the young cells had a short tail moment length. However, in the negative control group of the senescent cells (DMSO-treated groups), the tail moment length was increased and the cells became senescent, resulting in increased DNA damage. However, as compared to the control group (DMSO), the DNA damage significantly decreased in the presence of CP-466722. In FIG. 27, "HGPS p11" and "HGPS p17" respectively refer to "Hutchinson-Gilford Progeria Syndrome Skin Fibroblasts passages 11 and 17".

In addition, the influence of ATM-kinase inhibitor KU-466722 on the expression of SA-β-gal in the cells proliferated by the culture was confirmed by using a β-galactosidase staining kit (Cell Signaling Technology, #9860, Beverly, Mass.). According to the protocol of the manufacturer, a pH 6.0 X-gal chromogenic substrate was incubated overnight at a temperature of 37° C. to stain the cells having immobilized cell growth.

Figure 28:
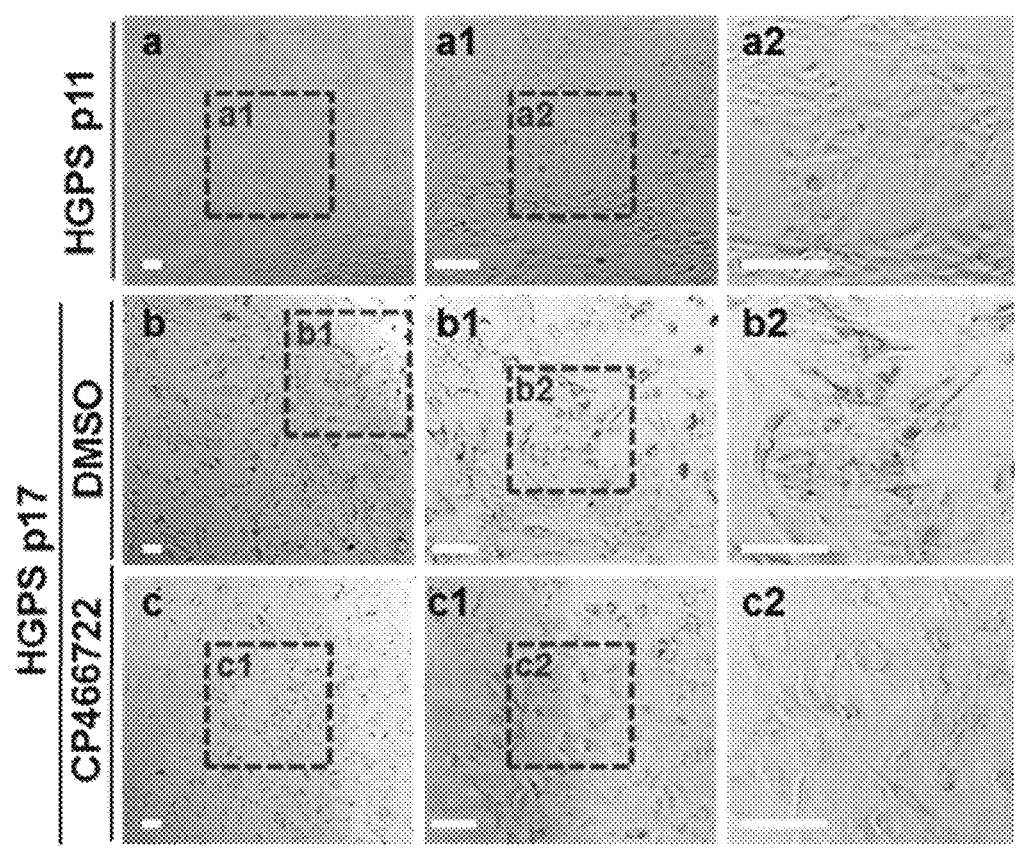
FIG. 28 is a view showing activity of SA-β-galactosidase of cells that are cultured in the presence of CP-466722 (0.1 µM)
Figure 29:
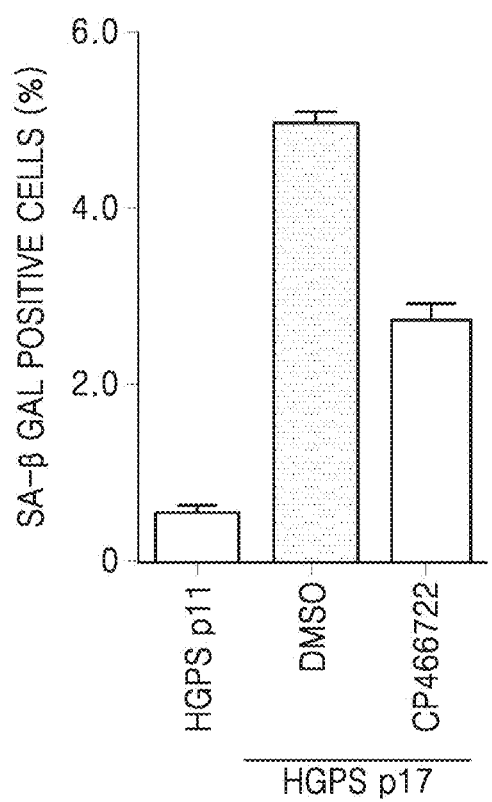
FIG. 29 is a graph showing a percentage of the cells of FIG. 28 having the activity of SA-β-galactosidase.

FIGS. 28 and 29 respectively are a view showing SA-β-gal activity of the cells that were cultured in the presence of CP-466722 (0.1 μM) (FIG. 29) and a graph showing a percentage of the cells having the SA-β-gal activity (FIG. 29). Referring to FIGS. 28 and 29, CP-466722 (0.1 μM) was added to a medium for culturing the progeria senescent fibroblasts (passage 17), and then, the cells were cultured in a $CO_2$ incubator at a temperature of 37° C. for 4 weeks. The medium was replaced by a fresh medium containing CP-466722 (0.1 μM), once every 4 days. As young cells, cells of passage 11, in which the cell doubling time was 6 to 7 days, were used. When culturing HPGS p11, HPGS p11 was cultured in DMSO without adding CP-466722 (0.1 μM) thereto. In addition, in the preparation of a negative control group, a medium containing DMSO (0.05 (v/v) %) was used under the same conditions described above. To provide a better view of the stained cells shown in the image a, a dashed square a1 was randomly selected, and then, the stained cells in the dashed square a1 are shown enlarged. To provide a better view of the stained cells shown in the dashed square a1, a dashed square a2 was randomly selected, and then, the stained cells in the dashed square a2 are shown enlarged (at a scale bar 20 μm). The same procedure applies similarly to the images b and c.

As shown in FIGS. 28 and 29, the number of cells that express β-galactosidase was very small in the young cells. However, number of cells that express β-galactosidase significantly increased in the negative control group (DMSO-treated group) of the senescent cells. That is, it was confirmed that the number of cells that express β-galactosidase, as compared to the control group (DMSO-treated group), significantly decreased in the presence of the compound, CP-466722.

(7) Influence of KU-60019 on Wound Healing (7.1) Materials and Methods

Wound healing assay, Immunohistochemistry, and Trichrome staining

To further test whether ATMi can promote cutaneous wounding healing in young (3 months old) and old (19 months old) male mice (C57BL/6J mice), four full-thickness punch-biopsy wounds (8 mm in diameter) were created on the dorsal skin of mouse (5 mice/experimental group), drug at a concentration of 5 μM KU-60019 in 30% Pluronic gel (Pluronic F-127 Sigma, P2443-1 KG) 0.5 mL was applied to wounds every day, and then covered the wounds with Telfa sponges (Kendall Health Care, Mansfield, Mass., USA). All animal studies were reviewed and approved by the International Animal Care and Use Committee of SKKU School of Medicine (SUSM). SUSM is an Association for Assessment and Accreditation of Laboratory Animal Care international accredited facility and abides by the Institute for Laboratory Animal Research guide. Wounds were photographed for 10 days. Immunohistochemistry analyses were performed on 5 μm paraffin embedded sections as described previously (Lin et. al., 2004. Developmental Biology 270, 474-486). Primary antibodies used for immunohistochemistry were mouse anti-α-smooth muscle actin (Sigma, F3777-2ML, 1:500), and mouse anti-PCNA (Santa Cruz Biotechnology, SC-56, 1:500). Secondary antibodies used for immunohistochemistry were EnVision™ Detection System (DAKO, K5007). Masson-Trichrome staining was performed according to the manufacturer's instructions (Polysciences Inc., Warrington Pa., USA).

(7.2) KU-60019 Treatment Plays an Important Role in Wound Healing

To further test whether KU-60019 can promote cutaneous wounding healing in young (3 months old) and old (19 months old) mice, we created full-thickness punch-biopsy wounds 8 mm in diameter on the dorsal skin of 10 mice (5 mice/each group), applied to the wounds at a concentration of 5 μM KU-60019 in 30% Pluronic gel (Pluronic F-127 Sigma, P2443-1 KG), and then covered the wounds with Telfa sponges (Kendall Health Care, Mansfield, Mass., USA). Pluronic F-127 is a hydrogel widely used in pharmaceuticals as a drug delivery vehicle for a variety of soluble mediators, including antibodies, cytokines, and growth factors. In young mouse (3 months old), macroscopic analyses of time-matched KU-60019-treated versus DMSO-treated wounds showed that closure is markedly accelerated at early time points during repair in KU-60019-treated wounds, with a mean of 87.6% of complete closure achieved by 7 day, compared with 74.1% closure in controls. Only 13.5% closure difference was shown between KU-60019-treated and DMSO-treated wounds. On the 9 day, wound healing was near completion in KU-60019-treated wounds, whereas DMSO-treated wounds still showed remnants of scabs. In old mouse (19 months old), macroscopic analyses of time-matched KU-60019-treated versus DMSO-treated wounds showed that closure is markedly accelerated at early time points during repair in KU-60019-treated wounds, with a mean of 69.4% of complete closure achieved by 7 day, compared with 49.4% closure in controls. 20% closure difference was shown between KU-60019-treated and DMSO-treated wounds. These data indicate that topical application of KU-60019 can expedite cutaneous wound healing in old mice, which showed the delayed wound healing in DMSO-treated group. On the 10 day, wound healing was near completion in KU-60019-treated wounds, whereas DMSO-treated wounds still showed remnants of scabs. KU-60019-treated wounds are capable of complete and efficient closure. It suggests that KU-60019 plays a pivotal role in wound repair, especially in old mice.

Figure 31:
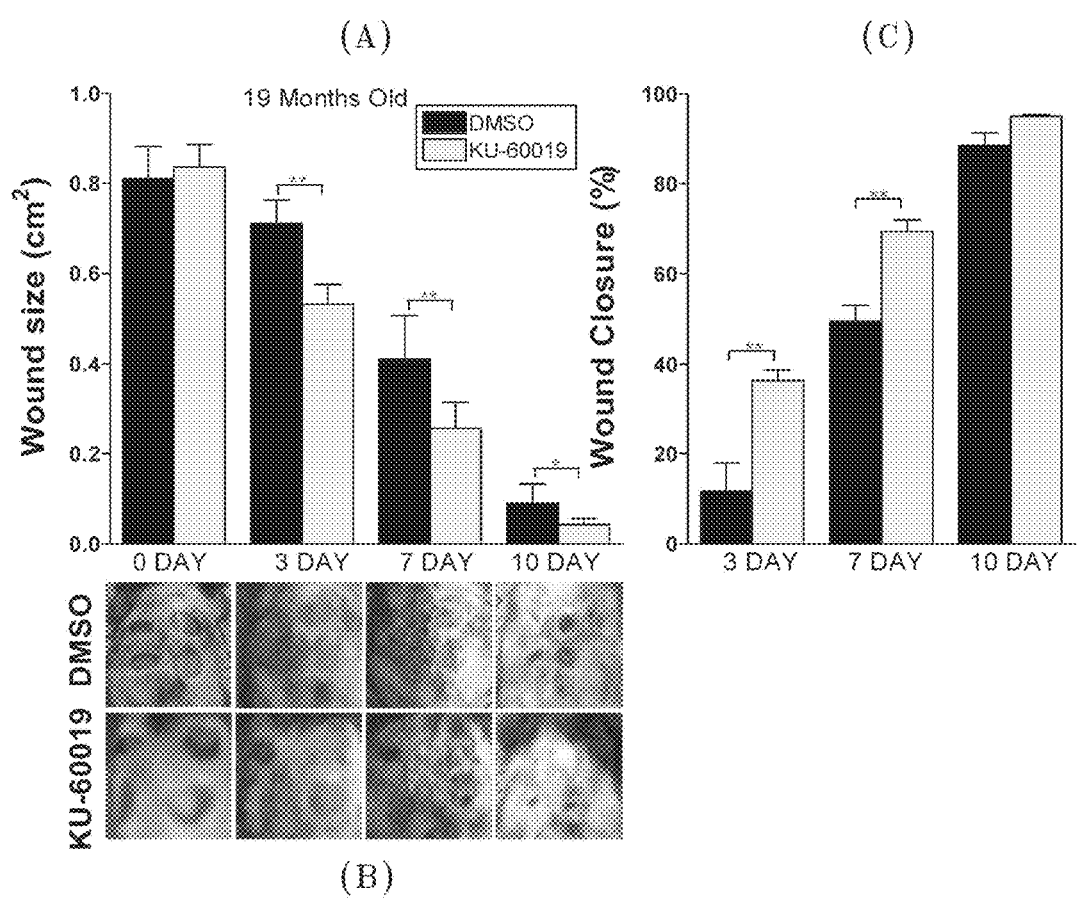
FIG. 31 presents experimental results showing that KU-60019 treatment plays an important role in wound healing in old mouse (19 months old: 19 mo).
Figure 32:
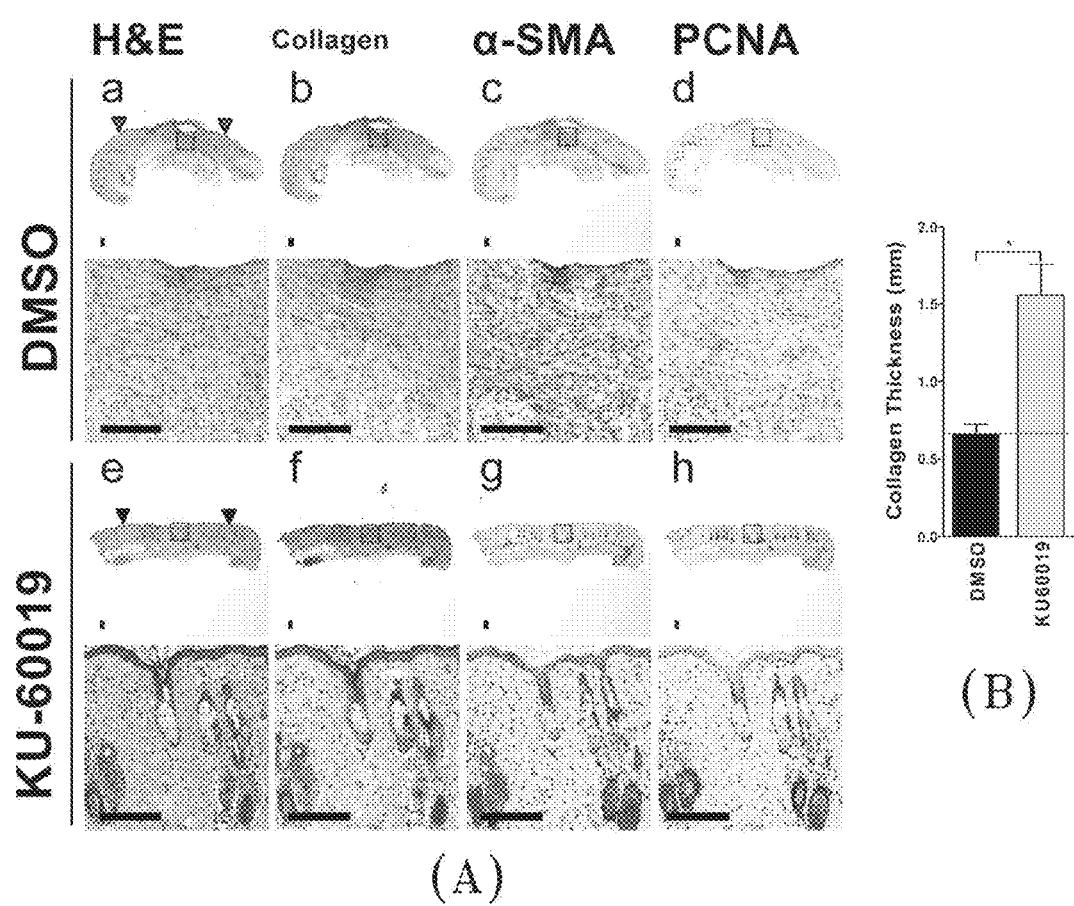
FIG. 32 and FIG. 33 each present experimental results showing that the sections of excisional wounds, which were stained with α-smooth muscle actin, showed that the myoblast staining was dense in the DMSO treated wounds in young (FIG. 32, panel A) and old mice (FIG. 33, panel A).

To find the exact mechanism during the wound healing process, the immunohistochemistry was done against several proteins. First, sections of excisional wounds were stained with α-smooth muscle actin, which is a marker of contractile myofibroblasts. Myofibroblasts were known to appear in the granulation tissue around the mid-phase of wound healing. The myoblast staining was dense in the DMSO treated wounds in young and old mice. The emergence of the myofibroblast phenotype (characterized by alpha-smooth muscle actin expression) means that fibrosis is undergoing in the wound healing area. However, ATMi-treated wounds showed the staining in the strong staining in epidermis suggesting that myofibroblasts may migrate to the epidermal region and the diffuse staining in the dermis area correlated with the concomitant appearance of collagen fiber in both young and old. Second, sections of excisional wounds were stained with Masson's Trichrome to reveal the gross collagen bundling patterns and the thickness of collagen deposition in the cross-sectional area of wound remodeling tissue. Advanced remodelling of the wound is defined by 100% collagen deposition in the wound gap (Braiman-Wiksman et al., 2007 Toxicologic Pathology 35, 767-779). The Masson's Trichrome staining revealed more dense and thicker collagen in the ATMi treated wounds compared to DMSO treated wounds (FIG. 31 and FIG. 32). Third, sections of excisional wounds were stained with PCNA, cellular marker for proliferation. Cutaneous wound healing is characterized by a proliferation phase, followed by maturation/remodeling phase showing the terminal differentiation of the newly formed epidermis. DMSO treated wounds shows the selective proliferation of the early granulation tissue, whereas the ATMi treated wounds shows the proliferation in the supra basal area of epidermis.

Figure 30:
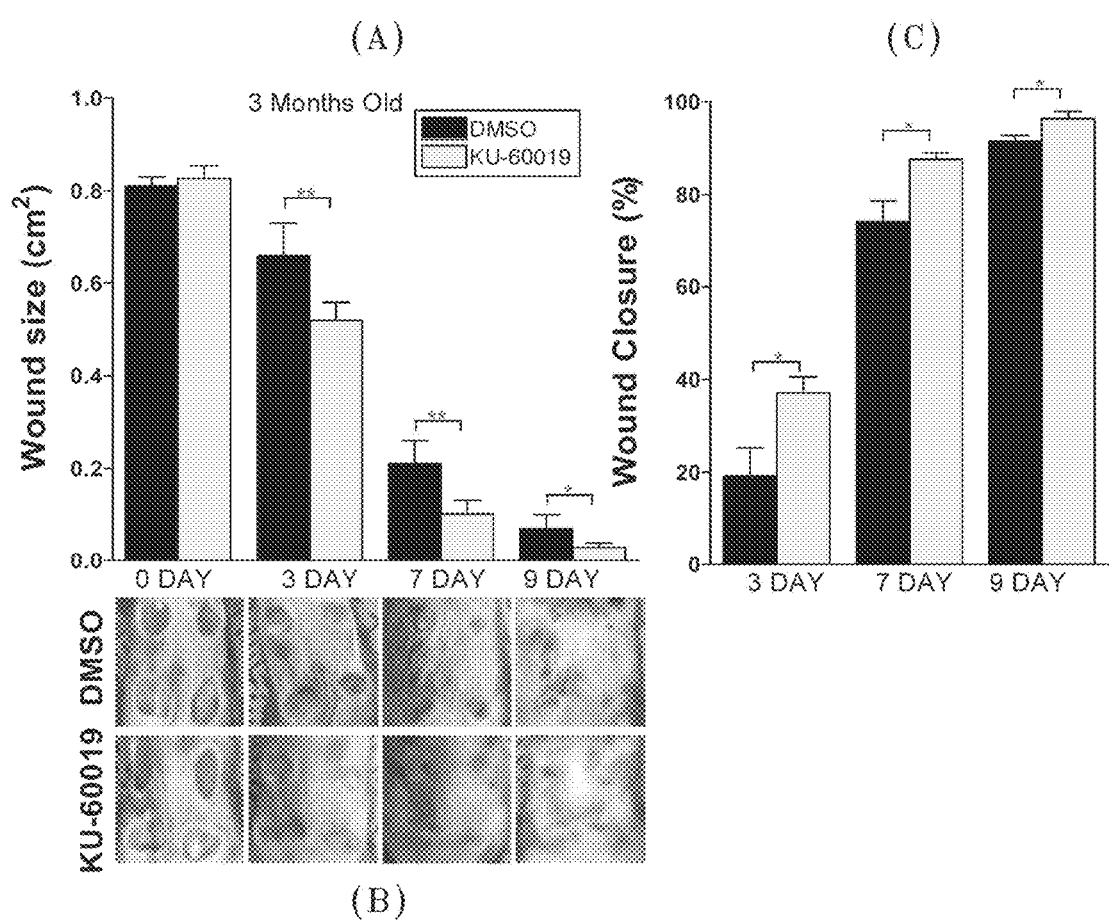
FIG. 30 presents experimental results showing that KU-60019 treatment plays an important role in wound healing in young mouse (3 months old: 3 mo).

FIG. 30 represents an experimental result showing that KU-60019 treatment plays an important role in wound healing in young mouse (3 months old: 3 mo). In young mouse (3 mo), macroscopic analyses of time-matched KU-60019-treated versus DMSO-treated wounds showed that closure is markedly accelerated at early time points during repair in KU-60019-treated wounds, with a mean of 87.6% of complete closure achieved by 7 day, compared with 74.1% closure in controls. Only 13.5% closure difference was shown between KU-60019-treated and DMSO-treated wounds. On the 9 day, wound healing was near completion in KU-60019-treated wounds, whereas DMSO-treated wounds still showed remnants of scabs.

FIG. 31 represents an experimental result showing that KU-60019 treatment plays an important role in wound healing in old mouse (19 months old: 19 mo). In old mouse (19 mo), macroscopic analyses of time-matched KU-60019-treated versus DMSO-treated wounds showed that closure is markedly accelerated at early time points during repair in KU-60019-treated wounds, with a mean of 69.4% of complete closure achieved by 7 day, compared with 49.4% closure in controls. 20% closure difference was shown between KU-60019-treated and DMSO-treated wounds. These data indicate that topical application of KU-60019 can expedite cutaneous wound healing in old mice, which showed the delayed wound healing in DMSO-treated group. On the 10 day, wound healing was near completion in KU-60019-treated wounds, whereas DMSO-treated wounds still showed remnants of scabs.

Figure 33:
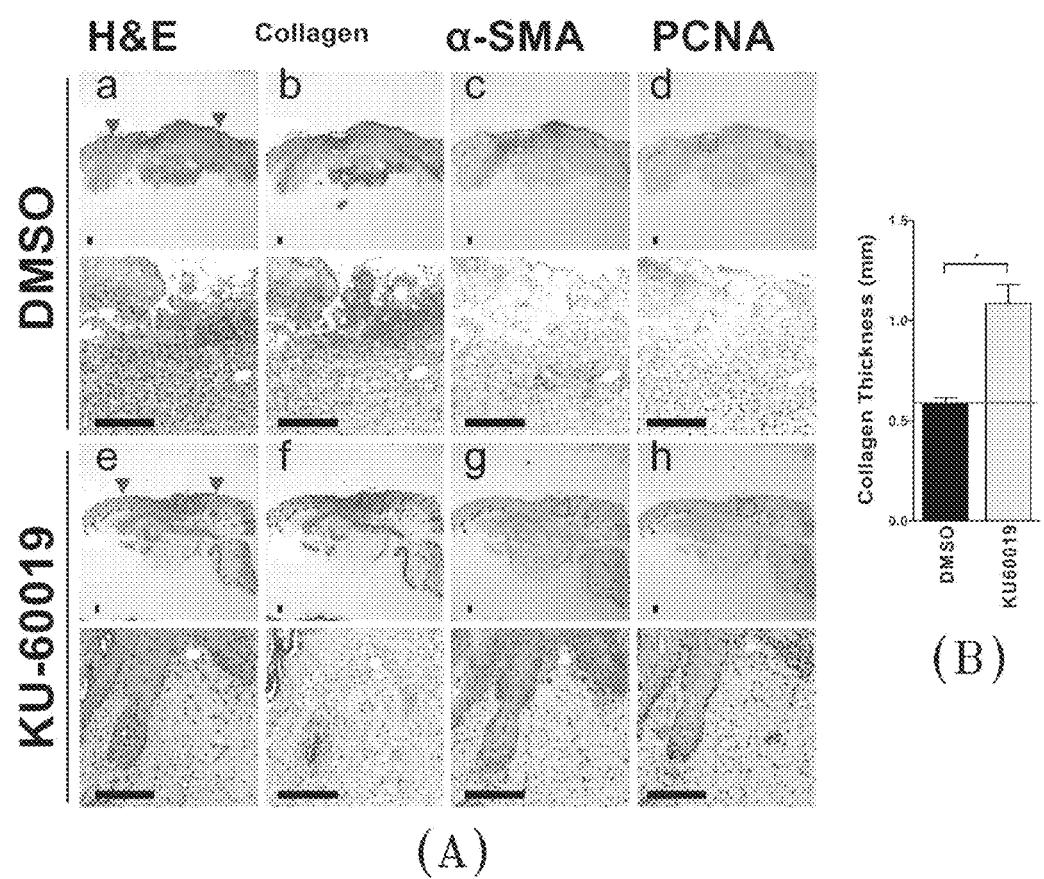

FIG. 32 and FIG. 33 represent experimental results showing that the sections of excisional wounds, which were stained with α-smooth muscle actin, showed that the myoblast staining was dense in the DMSO treated wounds in young (FIG. 32, A) and old mice (FIG. 33, A). The emergence of the myofibroblast phenotype (characterized by alpha-smooth muscle actin expression) means that fibrosis is undergoing in the wound healing area. However, ATMi-treated wounds showed the staining in the strong staining in epidermis suggesting that myofibroblasts may migrate to the epidermal region and the diffuse staining in the dermis area correlated with the concomitant appearance of collagen fiber in both young and old. Second, sections of excisional wounds were stained with Masson's Trichrome to reveal the gross collagen bundling patterns and the thickness of collagen deposition in the cross-sectional area of wound remodeling tissue. Advanced remodelling of the wound is defined by 100% collagen deposition in the wound gap. The Masson's Trichrome staining revealed more dense and thicker collagen in the ATMi treated wounds compared to DMSO treated wounds. Third, sections of excisional wounds were stained with PCNA, cellular marker for proliferation. Cutaneous wound healing is characterized by a proliferation phase, followed by maturation/remodeling phase showing the terminal differentiation of the newly formed epidermis. DMSO treated wounds shows the selective proliferation of the early granulation tissue, whereas the ATMi treated wounds shows the proliferation in the supra basal area of epidermis.

FIG. 32 and FIG. 33 represent experimental results showing that the thickness of collagen deposition in the cross-sectional area of wound remodeling tissue revealed more dense and thicker collagen in the ATMi treated wounds compared to DMSO treated wounds in young (FIG. 32, B) and old mice (FIG. 33, B).

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising,"

"having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of treating a wound in a mammal, the method comprising:
    administering an effective amount of an ataxia telangiectasia mutated (ATM) inhibitor to a mammal to treat the wound, wherein the ATM inhibitor is KU-60019, KU-55933, CP-466722, a pharmaceutically acceptable salt, a stereoisomer, or a combination thereof, wherein the ATM inhibitor enhances closure of the wound and reduces the size of the wound.

2. The method of claim 1, wherein the wound comprises a senescent cell.

* * * * *